US006593299B1

(12) United States Patent
Bennett et al.

(10) Patent No.: US 6,593,299 B1
(45) Date of Patent: Jul. 15, 2003

(54) COMPOSITIONS AND METHODS FOR CONTROLLING PESTS

(75) Inventors: John Bennett, Chapel Hill, NC (US); Alan Brandt, Chapel Hill, NC (US); Dov Borovsky, Vero Beach, FL (US)

(73) Assignees: University of Florida Research Foundation, Inc., Gainesville, FL (US); Insect Biotechnology, Inc., Durham, NC (US)

(*) Notice: Subject to any disclaimer, the term of this patent is extended or adjusted under 35 U.S.C. 154(b) by 0 days.

(21) Appl. No.: 09/295,924

(22) Filed: Apr. 21, 1999

(51) Int. Cl.[7] .................. A61K 38/00; A61K 38/04; A01N 37/18; C07K 16/00
(52) U.S. Cl. .................. 514/18; 514/2; 530/350; 530/300; 530/330
(58) Field of Search .................. 530/350, 300, 530/330; 514/2, 17, 18

(56) References Cited

U.S. PATENT DOCUMENTS

| | | | |
|---|---|---|---|
| 4,266,074 A | 5/1981 | Fujimoto et al. | 560/105 |
| 4,395,404 A | 7/1983 | Low et al. | 424/177 |
| 4,714,763 A | 12/1987 | Theodoropulos | 544/31 |
| 4,983,390 A | 1/1991 | Levy | 424/404 |
| 4,985,251 A | 1/1991 | Levy | 424/404 |
| 5,011,909 A | 4/1991 | Borovsky et al. | 530/328 |
| 5,093,362 A | 3/1992 | Milner et al. | 514/531 |
| 5,130,253 A | 7/1992 | Borovsky et al. | 435/320.1 |
| RE34,402 E | 10/1993 | Williams | 43/113 |
| 5,250,515 A | 10/1993 | Fuchs et al. | 514/12 |
| 5,259,153 A | 11/1993 | Olive et al. | 43/113 |
| 5,273,749 A | 12/1993 | Bok et al. | 424/405 |
| 5,344,821 A | 9/1994 | Kingan et al. | 514/12 |
| 5,348,665 A | 9/1994 | Schulte et al. | 210/748 |
| 5,358,934 A | 10/1994 | Borovsky et al. | 514/17 |
| 5,399,344 A | 3/1995 | Yang et al. | 424/84 |
| 5,428,147 A | 6/1995 | Barker et al. | 536/24.1 |
| 5,439,821 A | 8/1995 | Borovsky et al. | 435/240.4 |
| 5,459,130 A | 10/1995 | Borovsky et al. | 514/17 |
| 5,501,976 A | 3/1996 | Borovsky et al. | 435/252.3 |
| 5,513,465 A | 5/1996 | Demarest et al. | 43/113 |
| 5,522,171 A | 6/1996 | Mandeville | 43/122 |
| 5,527,883 A | 6/1996 | Thompson et al. | 530/350 |
| 5,567,430 A | 10/1996 | Levy | 424/409 |
| 5,604,121 A | 2/1997 | Hilder et al. | 435/172.3 |
| 5,612,047 A | 3/1997 | Duffy et al. | 424/405 |
| 5,629,196 A | 5/1997 | Borovsky et al. | 435/418 |
| 5,656,260 A | 8/1997 | Boden et al. | 424/84 |
| 5,670,145 A | 9/1997 | Wright | 424/84 |
| 5,676,846 A | 10/1997 | Vickell et al. | 210/759 |
| 5,676,958 A | 10/1997 | Emerson et al. | 424/405 |
| 5,683,687 A | 11/1997 | Marin et al. | 424/84 |
| 5,688,764 A | 11/1997 | Johnson et al. | 514/12 |
| 5,693,344 A | 12/1997 | Knight et al. | 424/687 |
| 5,713,153 A | 2/1998 | Cook et al. | 43/114 |
| 5,714,191 A | 2/1998 | Hatton et al. | 426/532 |
| 5,737,870 A | 4/1998 | Thind | 43/107 |
| 5,741,669 A | 4/1998 | Krapcho et al. | 435/69.1 |
| 5,749,168 A | 5/1998 | Chrysanthis | 43/122 |
| 5,753,615 A | 5/1998 | Thorpe et al. | 514/2 |
| 5,792,750 A | 8/1998 | Borovsky et al. | 514/6 |
| 5,800,811 A | 9/1998 | Hall et al. | 424/93.7 |
| 5,824,328 A | 10/1998 | Levy | 424/409 |
| 5,840,293 A | 11/1998 | Nacht et al. | 424/78.02 |
| 5,846,553 A | 12/1998 | Levy | 424/409 |
| 5,849,525 A | 12/1998 | Hediger | |

FOREIGN PATENT DOCUMENTS

| | | |
|---|---|---|
| EP | 0 682 115 | 9/1989 |
| EP | 0 412 595 | 2/1991 |
| JP | 01226898 | 9/1989 |
| JP | 07188282 | 7/1995 |
| WO | WO93/21217 | 10/1993 |
| WO | WO94/13698 | 6/1994 |
| WO | WO00/18920 | 4/2000 |

OTHER PUBLICATIONS

Masuda et al., 1991; Eur. J. Biochem. 202:783–787.*
Voit et al. 1990; J. Biol. Chem. 265(39):19477–19452.*
Janssen, I. et al. "Biological Activity of Structural Analogs and Efect of Oil as a Carrier of Trypsin Modulating Oostatic Factor of the Gray Fleshfly *Neobellieria bullata*," Peptides 19(4): 627–634 (1998).
Masoud, S.A., et al. "Expression of a cysteine proteinase inhibitor (oryzacystatin–I) in transgenic tobacco plants," Plant Molecular Biology 21:655–663, 1993.
Hua, Y–J., Koolman, J., "An ecdysiostatin from flies," Regulatory Peptides 57: 263–271 (1995).
Dahlen, J.R., et al. "Expression, Purification and Inhibitory Properties of Human Proteinase Inhibitor," Biochemistry 1997, 35: 14874–14882.
Bylemans, D., et al. "Immunolocalization of the Oostatic and Prothoracicostatic Peptide, Neb–TMOF, in Adults of the fleshfly, *Neobellieria bullata*. " General and Comparative Endocrinology 103: 273–280 (1996).
Borovsky, D., et al., "Molecular sequencing and modeling of *Neobellieria bullata* trypsin. Evidence for translational control by Neobellieria trypsin–modulating oostatic factor."Eur. J. Biochem 237: 279–287 (1996).
Bylemans, D., et al. "Neb–colloostatin, a second folliculostatin of the grey fleshfly, *Neobellieria bullata*." Eur. J. Biochem 228: 45–49.
Borovsky, D., "Physiological and Biochemical Studies of Trypsin Modulating Oostatic Factor (TMOF) in Insects." Project statement—Investigative study, University of Florida Oct. 1, 1993–Sep. 30, 1998.

(List continued on next page.)

*Primary Examiner*—Karen Cochrane Carlson
(74) *Attorney, Agent, or Firm*—Steven J. Hultquist; Marianne Fuierer; Yongzhi Yang

(57) ABSTRACT

Novel pest control compounds, compositions comprising such compounds, and methods for using such compounds and compositions against a variety of pests, including pests of agricultural crops.

38 Claims, 3 Drawing Sheets

OTHER PUBLICATIONS

Figure 1:
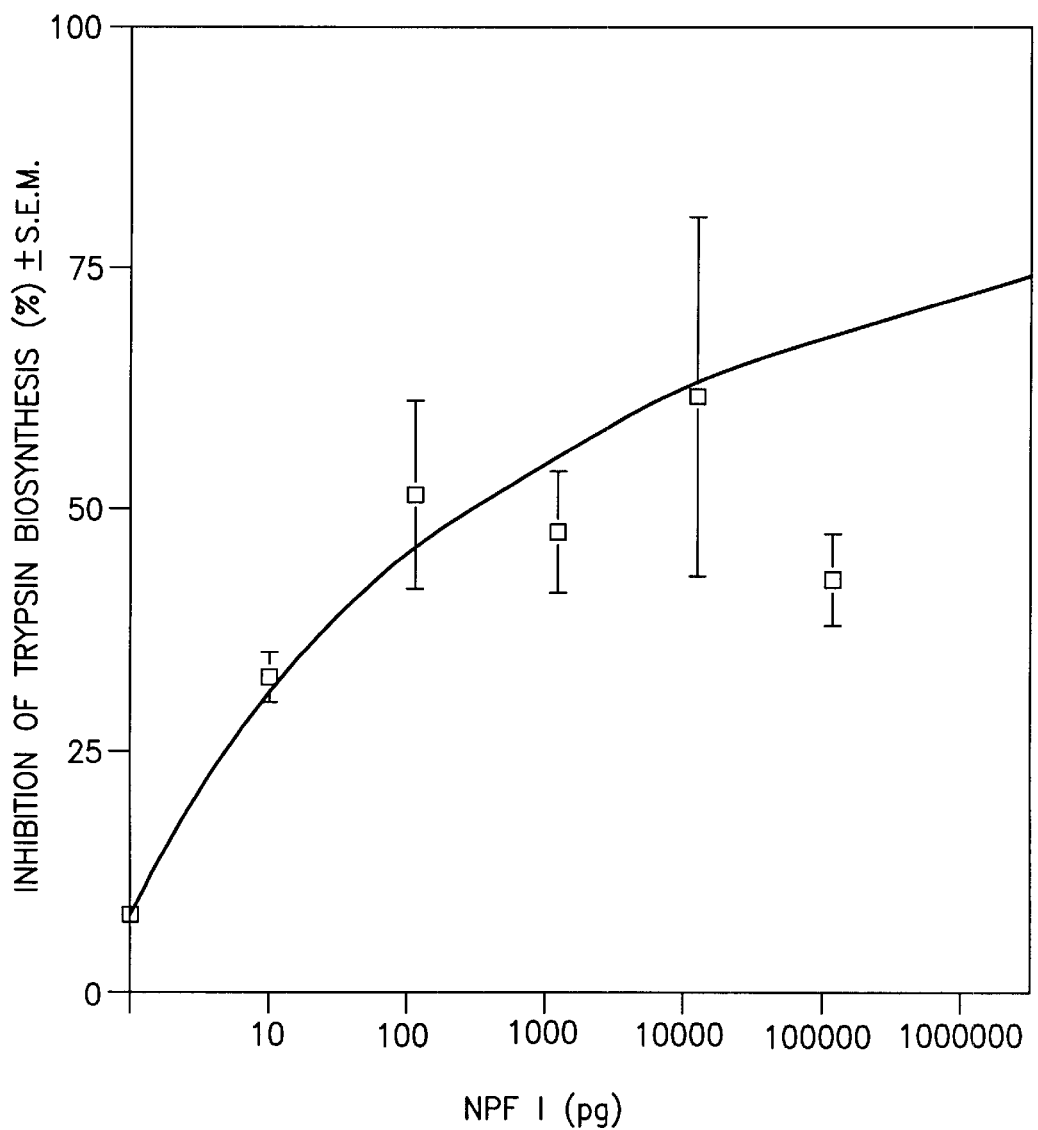

Bylemans, et al., "Sequencing and characterization of trypsin modulating oostatic factor (TMOF) from the ovaries of the grey fleshfly, *Neobellieria (Sarcophaga) bullata.*" Regulatory Peptides 50: 61–72 (1994).

Lin, Y., et al. "Structure, Expression and Hormonal Control of Genes from the Mosquito, *Aedes aegypti*, Which Encode Proteins Similar to the Vitelline Membrane Proteins of *Drosophila melanogaster.*" Developmental Biology 155: 558–568 (1993).

Vaeck, M., et al. "Transgenic plants protected from insect attack." Nature 328: 33–37 (1987).

Taylor, M., "Trypsin Isolated from the Midgut of the Tobacco Hornworm, *Manduca sexta*, I Inhibited by Synthetic Pro–peptides in Vitro." Biochemical and Biophysical Research Communications, 235: 606–609 (1997).

Southwick, FS and D.L. Purich, "Inhibition of Listeria Locomotion by Mosquito Oostatic Factor, a Natural Oligoproline Peptide Uncoupler of Profilin Action." Infection and Immunity, 63(1): 82–190 1995.

Borovsky, "Feeding the mosquito *Aedes aegypti* with TMOF and its analogs; effect on trypsin biosynthesis and egg development." Regulatory Peptides, (57) 273–281, 1995.

Hlavacek et al, "The C–Terminus Shortened Analogs of the Insect Peptide Oostatic Hormone with Accelerated Activity", Bioorganic Chemistry, (26), p. 131–140, 1998.

Okada et al., 87: 146142, Synthesis of bradykinin fragments and their effect on pentobarbital sleeping time in mouse. Neuropharmacology 1977 16(5), 381–3. (abstract only).

Shibnev et al., 115551t "Synthesis of monomers that are triplets of the "crystalline" part of the collagen molecule." Izv.Adad. Nauk SSSR, Ser. Khim, 1969, 2 392–7 (abstract only).

Narberhaus et al., "The bradyrhizobium japonicum rpoH1 gene encoding a sigma 32–like protein is part of a . . . " J. Bacteriol. 178 (18), 5337–5346 (1996) (abstract only).

Gauthier et al., "A flavonol 3'/5'—O–methyltransferase cDNA clone . . . " Plant Physiol. 108 (3), 1341 (1995) (abstract only).

Borovsky et al. "Mass spectrometry and characterization of *Aedes aegypti* trypsin modulating oostatic factor (TMOF) and its analogs." Insect Biochem. Molec. Biol. vol. 23, No. 6, patent 703–712, 1993.

Borovsky. "Isolation and characterization of highly purified mosquito oostatic hormone." Archives of Insect Biochemistry and Physiology 2:333–349 (1985).

Borovsky. "Oostatic hormone inhibits biosynthesis of midgut proteolytic enzymes and egg development in mosquitoes." Archives of Insect Biochemistry and Physiology 7: 187–210 (1988).

Borovsky et al. "Mosquito oostatic factor: a novel decapeptide modulating trypsin–like enzyme biosynthesis in the midgut." The FASEB Journal. vol. 4, Sep. 1990.

Borovsky et al. "Characterization and localization of mosquito–gut receptors for trypsin modulating oostatic factor using a complementary peptide and immunocytochemistry." The FASEB Journal. vol. 8. 350–355 Mar. 1994.

Borovsky et al. "Feeding the mosquito *Aedes aegypti* with TMOF and its analogs; effect on trypsin biosynthesis and egg development." Regulatory Peptides 57 (1995) 273–281.

Curry et al. "Neuropeptide F: primary structure from the tubellarian, Artioposthia Triangulata." Comp. Biochem. Physiol. vol. 101C No. 2, 269–274, 1992.

Duve et al. "Isolation and partial characterization of pancreatic polypeptide–like material in the brain of the blowfly *Calliphora vomitoria.*" Biochem J. (1981) 197, 767–770.

Leung et al. "The primary structure of neuropeptide F (NPF) from the garden snail, *Helix aspersa.*" ++++ Peptides, 1 (1992) 71–81.

Maule et al. "Neuropeptide F: a novel parasitic flatworm regulatory peptide from Moniezia expansa (Cestoda: Cyclophyllidea)." Parasitology (1991) 102: 309–316.

Rajpara et al. "Identification and molecular cloning of a neuropeptide Y homolog that produces prolonged inhibition in Aplysia neurons." Neuron, vol. 9, 505–513. Sep. 1992.

Spittaels et al. "Insect neuropeptide F (NPF)–related peptides: isolation from Colorado Potato Beetle (*Leptinotarsa decemlineata*) Brain." Insect Biochem Molec Biol. vol. 26, No. 4, 375–382, 1996.

Veenstra et al. "Immunocytochemical localization of peptidergic neurons and neurosecretory cells in the neuro–endocrine system of the Colorado potato beetle with antisera to vertebrate regulatory peptides." Histochemistry (1985) 82: 9–18.

Verhaert et al. "Distinct localization of FMRFamide– and bovine pancreatic polypeptide–like material in the brain, retrocerebral complex and suboesophageal ganglion of the cockroach Periplaneta Americana L." Brain Research, 348 (1985) 331–338.

Shibnev et al. "Synthesis of monomers that are triplets of "crystalline" part of the collagen molecule." Insec. Molec. Biol. 1969, (2), 392–7. (abstract only).

Henderson et al. "Physiochemical studies of biologically active peptides by low–temperature reversed–phase high–performance liquid chromatography." J. Chromatography. 1990, 499, 79–88. (abstract only).

Okada et al. "Synthesis of bradykinin fragments and their effect on pentobarbital sleeping time in mouse." Pharmacology, 1977, 16, 381–383.

Ladram et al. "Characterization of receptors for thyrotropin–releasing hormone–potentiating peptide on rat anterior pituitary membranes." The Jour. Of Biol. Chem. vol. 267, No. 36, 25697–25702, 1992.

Bordusa et al. "The specificity of prolyl endopeptidase from *Flavobacterium meningoseptum*: mapping the S' subsites by positional scanning via Acyl transfer." Bio. & Med. Chem 6 (1998) 1775–1780.

Deslauriers et al. "Steric effects of cis–trans isomerism on neighboring reidues in proline oligopeptides: A$^{13}$C–NMR study of conformational heterogeneity in linear tripeptides." Biopolymers, vol. 18, 523–538 (1979).

Kolaskar et al. "Conformational properties of pairs of amino acids." Int. J. Peptide Protein Res. 22, 1983, 83–91.

Richard, et al. "The fate of an oostatic peptide or its analogs including metabolites in insects Diptera and Orthoptera and its transformation to the next generation." Collect. Symp. Ser. 1999, 3, 57–60. (abstract only).

Borovsky et al. "Development of specific RIA and ELISA to study trypsin modulating oostatic factor in mosquitoes." Archives of Insect Biochemistry and Physiology 21: 13–21 (1992).

Merkler et al. "C–terminal amidated peptides: production by the in vitro enzymatic amidation of glycine–extended peptides and the importance of the amide to bioactivity." Enzyme Microb. Technol., 1994, vol. 16, Jun.

Pauletti et al. "Structural requirements for intestinal absorption of peptide drugs." Jour. Of Controlled Release 41 (1996) 3–17.

Rudinger. "Characteristics of the amino acids as components of a peptide hormone sequence."

Barberhaus et al. "Small Heat Shock Protein HSPB." NCBI. May 30, 2000.

Gauthier et al. "3' flavonoid O–methyltransf . . . " NCBI. Nov. 6, 1995.

Hlavacek et al. "The C–terminus shortened analogs of the insect peptide oostatic hormone with accelerated activity." Bioorganic Chem. 26, 131–140 (1998).

* cited by examiner

SEQUENCE LISTING

```
<160> NUMBER OF SEQ ID NOS: 54

<210> SEQ ID NO 1
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Truncated TMOF

<400> SEQUENCE: 1

Tyr Asp Pro Ala Pro
1               5

<210> SEQ ID NO 2
<211> LENGTH: 6
<212> TYPE: PRT
<213> ORGANISM: Artificial Sequence
<220> FEATURE:
<221> NAME/KEY: misc_feature
<222> LOCATION: ()..()
<223> OTHER INFORMATION: Truncated TMOF

<400> SEQUENCE: 2
```

Tyr Asp Pro Ala Pro Pro
1               5

<210> SEQ ID NO 3
<211> LENGTH: 7
<212> TYPE: PRT
<213> ORGANISM: Artificial Sequence
<220> FEATURE:
<221> NAME/KEY: misc_feature
<222> LOCATION: ()..()
<223> OTHER INFORMATION: Truncated TMOF

<400> SEQUENCE: 3

Tyr Asp Pro Ala Pro Pro Pro
1               5

<210> SEQ ID NO 4
<211> LENGTH: 8
<212> TYPE: PRT
<213> ORGANISM: Artificial Sequence
<220> FEATURE:
<221> NAME/KEY: misc_feature
<222> LOCATION: ()..()
<223> OTHER INFORMATION: Truncated TMOF

<400> SEQUENCE: 4

Tyr Asp Pro Ala Pro Pro Pro Pro
1               5

<210> SEQ ID NO 5
<211> LENGTH: 10
<212> TYPE: PRT
<213> ORGANISM: Leptinotarsa decemlineata

<400> SEQUENCE: 5

Ala Arg Gly Pro Gln Leu Arg Leu Arg Phe
1               5                   10

<210> SEQ ID NO 6
<211> LENGTH: 6
<212> TYPE: PRT
<213> ORGANISM: Leptinotarsa decemlineata

<400> SEQUENCE: 6

Ala Pro Ser Arg Leu Arg
1               5

<210> SEQ ID NO 7
<211> LENGTH: 10
<212> TYPE: PRT
<213> ORGANISM: Aedes sp.

<400> SEQUENCE: 7

Tyr Asp Pro Ala Pro Pro Pro Pro Pro Pro
1               5                   10

<210> SEQ ID NO 8
<211> LENGTH: 10
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 8

Asp Tyr Pro Ala Pro Pro Pro Pro Pro

```
1               5               10

<210> SEQ ID NO 9
<211> LENGTH: 9
<212> TYPE: PRT
<213> ORGANISM: Artificial Sequence
<220> FEATURE:
<221> NAME/KEY: misc_feature
<222> LOCATION: ()..()
<223> OTHER INFORMATION: Truncated TMOF

<400> SEQUENCE: 9

Pro Ala Pro Pro Pro Pro Pro Pro Pro
1               5

<210> SEQ ID NO 10
<211> LENGTH: 6
<212> TYPE: PRT
<213> ORGANISM: Artificial Sequence
<220> FEATURE:
<223> OTHER INFORMATION: Truncated TMOF

<400> SEQUENCE: 10

Asn Pro Thr Asn Leu His
1               5

<210> SEQ ID NO 11
<211> LENGTH: 4
<212> TYPE: PRT
<213> ORGANISM: Artificial Sequence
<220> FEATURE:
<221> NAME/KEY: misc_feature
<222> LOCATION: ()..()
<223> OTHER INFORMATION: Flanking proline residues

<400> SEQUENCE: 11

Pro Pro Pro Pro
1

<210> SEQ ID NO 12
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Flanking proline residues

<400> SEQUENCE: 12

Pro Pro Pro Pro Pro
1               5

<210> SEQ ID NO 13
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 13

Ala Ala Pro
1

<210> SEQ ID NO 14
<211> LENGTH: 3
<212> TYPE: PRT
```

```
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 14

Ala Asp Pro
1

<210> SEQ ID NO 15
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 15

Ala Asp Pro Ala Pro
1               5

<210> SEQ ID NO 16
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 16

Ala Pro Ala
1

<210> SEQ ID NO 17
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 17

Asp Ala Ala
1

<210> SEQ ID NO 18
<211> LENGTH: 2
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 18

Asp Phe
1

<210> SEQ ID NO 19
<211> LENGTH: 3
<212> TYPE: PRT
<213> ORGANISM: Artificial Sequence
<220> FEATURE:
<221> NAME/KEY: misc_feature
<222> LOCATION: ()..()
```

```
<223> OTHER INFORMATION: TMOF analog

<400> SEQUENCE: 19

Asp Pro Ala
1

<210> SEQ ID NO 20
<211> LENGTH: 2
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 20

Asp Tyr
1

<210> SEQ ID NO 21
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 21

Asp Tyr Pro
1

<210> SEQ ID NO 22
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 22

Phe Ala Pro
1

<210> SEQ ID NO 23
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 23

Phe Asp Pro
1

<210> SEQ ID NO 24
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 24
```

```
Phe Asp Pro Ala Pro
1               5

<210> SEQ ID NO 25
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 25

Phe Ser Pro
1

<210> SEQ ID NO 26
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 26

Pro Ala Ala
1

<210> SEQ ID NO 27
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 27

Pro Ala Pro
1

<210> SEQ ID NO 28
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 28

Pro Ala Pro
1

<210> SEQ ID NO 29
<211> LENGTH: 4
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog
<221> NAME/KEY: MOD_RES
<222> LOCATION: (2)..(2)
<223> OTHER INFORMATION: dextrorotary amino acid

<400> SEQUENCE: 29

Tyr Asp Asp Pro
```

```
<210> SEQ ID NO 30
<211> LENGTH: 6
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog
<221> NAME/KEY: MOD_RES
<222> LOCATION: (2)..(2)
<223> OTHER INFORMATION: dextrorotary amino acid

<400> SEQUENCE: 30

Tyr Asp Asp Pro Ala Pro
1               5

<210> SEQ ID NO 31
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 31

Tyr Ala Pro
1

<210> SEQ ID NO 32
<211> LENGTH: 2
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 32

Tyr Asp
1

<210> SEQ ID NO 33
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 33

Tyr Asp Ala
1

<210> SEQ ID NO 34
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 34

Tyr Asp Ala Ala Pro
1               5
```

```
<210> SEQ ID NO 35
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 35

Tyr Asp Phe
1

<210> SEQ ID NO 36
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 36

Tyr Asp Phe Ala Pro
1               5

<210> SEQ ID NO 37
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 37

Tyr Asp Gly
1

<210> SEQ ID NO 38
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 38

Tyr Asp Leu Ala Pro
1               5

<210> SEQ ID NO 39
<211> LENGTH: 3
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 39

Tyr Asp Pro
1

<210> SEQ ID NO 40
<211> LENGTH: 4
```

```
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog
<221> NAME/KEY: MOD_RES
<222> LOCATION: (1)..(1)
<223> OTHER INFORMATION: dextrorotary amino acid

<400> SEQUENCE: 40

Asp Tyr Asp Pro
1

<210> SEQ ID NO 41
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 41

Tyr Asp Pro Ala Phe
1               5

<210> SEQ ID NO 42
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 42

Tyr Asp Pro Ala Leu
1               5

<210> SEQ ID NO 43
<211> LENGTH: 6
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog
<221> NAME/KEY: MOD_RES
<222> LOCATION: (1)..(1)
<223> OTHER INFORMATION: dextrorotary amino acid

<400> SEQUENCE: 43

Asp Tyr Asp Pro Ala Pro
1               5

<210> SEQ ID NO 44
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 44

Tyr Asp Pro Phe Pro
1               5
```

```
<210> SEQ ID NO 45
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 45

Tyr Asp Pro Gly Pro
1               5

<210> SEQ ID NO 46
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 46

Tyr Asp Pro Leu Pro
1               5

<210> SEQ ID NO 47
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 47

Tyr Glu Pro Ala Pro
1               5

<210> SEQ ID NO 48
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 48

Tyr Phe Pro Ala Pro
1               5

<210> SEQ ID NO 49
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 49

Tyr Asn Pro Ala Pro
1               5

<210> SEQ ID NO 50
<211> LENGTH: 3
<212> TYPE: PRT
<213> ORGANISM: Artificial Sequence
```

```
<220> FEATURE:
<221> NAME/KEY: misc_feature
<222> LOCATION: ()..()
<223> OTHER INFORMATION: TMOF analog

<400> SEQUENCE: 50

Tyr Ser Phe
1

<210> SEQ ID NO 51
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 51

Tyr Ala Pro Ala Pro
1               5

<210> SEQ ID NO 52
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 52

Tyr Ser Pro Ala Pro
1               5

<210> SEQ ID NO 53
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 53

Tyr Asp Pro Ala Ala
1               5

<210> SEQ ID NO 54
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: TMOF analog

<400> SEQUENCE: 54

Ala Asp Ala Ala Pro
1               5
```

COMPOSITIONS AND METHODS FOR CONTROLLING PESTS

This application incorporates by reference the entire disclosures of the following co-filed U.S. patent applications: U.S. patent application Ser. No. 09/295,849 "Neuropeptides and Their Use for Pest Control"; U.S. patent application Ser. No. 09/295,846 "Transformed Cells Useful for the Control of Pests"; U.S. patent application Ser. No. 09/296,113 "Materials and Methods Useful for the Control of Insect Larvae"; and U.S. patent application Ser. No. 09/295,996 "Novel Peptides and the Use Thereof to Control Pests"; all co-filed with the present application on Apr. 21, 1999.

1. BACKGROUND OF THE INVENTION

Many blood-ingesting pests are known to feed on humans and animals, and many pests are vectors for pathogenic microorganisms which threaten human and animal health, including commercially important livestock, pets and other animals. Various species of mosquitoes, for example, transmit diseases caused by viruses, and many are vectors for disease-causing nematodes and protozoa. Mosquitoes of the genus Anopheles transmit Plasmodium, the protozoan which causes malaria, a devastating disease which results in approximately 1 million deaths annually. The mosquito species *Aedes aegypti* transmits an arbovirus that causes yellow fever in humans. Other arboviruses transmitted by Aedes species include the causative agents of dengue fever, eastern and western encephalitis, Venezuelan equine encephalitis, St. Louis encephalitis, chikungunya, oroponehe and bunyarnidera. The genus Culex, which includes the common house mosquito *C. pipiens*, is implicated in the transmission of various forms of encephalitis and filarial worms. The common house mosquito also transmits *Wuchereria banuffi* and *Brugia malayi*, which cause various forms of lymphatic filariasis, including elephantiasis. *Trypanasomas cruzi*, the causative agent of Chagas' disease, is transmitted by various species of blood-ingesting Triatominae bugs. The tsetse fly (Glossina spp.) transmits African trypanosomal diseases of humans and cattle. Many other diseases are transmitted by various blood-ingesting pest species. The order Diptera contains a large number of blood-ingesting and disease-bearing insects, including, for example, mosquitoes, black flies, no-see-ums (punkies), horse flies, deer flies and tsetse flies.

Various pesticides have been employed in efforts to control or eradicate populations of disease-bearing pests, such as disease-bearing blood-ingesting. pests. For example, DDT, a chlorinated hydrocarbon, has been used in attempts to eradicate malaria-bearing mosquitoes throughout the world. Other examples of chlorinated hydrocarbons are BHC, lindane, chlorobenzilate, methoxychlor, and the cyclodienes (e.g., aldrin, dieldrin, chlordane, heptachlor, and endrin). The long-term stability of many of these pesticides and their tendency to bioaccumulate render them particularly dangerous to many non-pest organisms.

Another common class of pesticides is the organophosphates, which is perhaps the largest and most versatile class of pesticides. Organophosphates include, for example, parathion, Malathion™, diazinon, naled, methyil parathion, and dichlorvos. Organophosphates are generally much more toxic than the chlorinated hydrocarbons. Their pesticidal effect results from their ability to inhibit the enzyme cholinesterase, an essential enzyme in the functioning of the insect nervous system. However, they also have toxic effects on many animals, including humans.

The carbamates, a relatively new group of pesticides, include such compounds as carbamyl, methomyl, and carbofuran. These compounds are rapidly detoxified and eliminated from animal tissues. Their toxicity is thought to involve a mechanism similar to the mechanism of the organophosphates; consequently, they exhibit similar shortcomings, including animal toxicity.

A major problem in pest control results from the capability of many species to develop pesticide resistance. Resistance results from the selection of naturally-occurring mutants possessing biochemical, physiological or behavioristic factors that enable the pests to tolerate the pesticide. Species of Anopheles mosquitoes, for example, have been known to develop resistance to DDT and dieldrin. DDT substitutes, such as Malathion™, propoxur and fenitrothion are available; however, the cost of these substitutes is much greater than the cost of DDT.

There is clearly a longstanding need in the art for pesticidal compounds that are pest-specific, that reduce or eliminate direct and/or indirect threats to human health posed by presently available pesticides, that are environmentally compatible in the sense that they are biodegradable, and are not toxic to non-pest organisms, and have reduced or no tendency to bioaccummulate.

Many pests, including for example blood-inbibing pests, must consume and digest a proteinaceous meal to acquire sufficient essential amino acids for growth, development and the production of mature eggs. Adult pests, such as adult mosquitoes, need these essential amino acids for the production of vitellogenins by the fat body. These vitellogenins are precursors to yolk proteins which are critical components of oogenesis. Many pests, such as house flies and mosquitoes, produce oostatic hormones that inhibit egg development by inhibiting digestion of the protein meal, and thereby limiting the availability of the essential amino acids necessary for egg development.

Serine esterases such as trypsin and trypsin-like enzymes (collectively referred to herein as "TTLE") are important components of the digestion of proteins by insects. In the mosquito, *Aedes aegypti*, an early trypsin that is found in the midgut of newly emerged females is replaced, following the blood meal, by a late trypsin. A female mosquito typically weighs about 2 mg and produces 4 to 6 $\mu$g of trypsin within several hours after a ingesting blood meal. Continuous boisynthesis at this rate would exhaust the available metabolic energy of a female mosquito; as a result, the mosquito would be unable to produce mature eggs, or even to find an oviposition site. To conserve metabolic energy, the mosquito regulates TTLE biosynthesis with a peptide hormone named Trypsin Modulating Oostatic Factor (TMOF). TMOF mosquitoes produce in the follicular epithelium of the ovary 12–35 hours after a blood meal; TMOF is then released into the hemolymph where it binds to a specific receptor on the midgut epithelial cells, signaling the termination of TTLE biosynthesis.

This regulatory mechanism is not unique for mosquitoes; flesh flies, fleas, sand flies, house flies, dog flies and other insect pests which need protein as part of their diet have similar regulatory mechanisms.

In 1985, Borovsky purified an oostatic hormone 7,000-fold and disclosed that injection of a hormone preparation into the body cavity of blood imbibed mosquitoes caused inhibition of egg development and sterility (Borovsky, D. [1985] *Arch. Insect Biochem. Physiol.* 2:333–349). Following these observations, Borovsky (Borovsky, D. [1988] *Arch. Ins. Biochem. Physiol.* 7:187–210) reported that injection or passage of a peptide hormone preparation into mosquitoes inhibited the TTLE biosynthesis in the epithelial cells of the gut. This inhibition caused inefficient digestion of the blood meal and a reduction in the availability of essential amino acids translocated by the hemolymph, resulting in arrested egg development in the treated insect. Borovsky observed that this inhibition of egg development does not occur when the oostatic hormone peptides are inside the lumen of the gut or other parts of the digestive system (Borovsky, D. [1988], supra).

Following the 1985 report, the isolated hormone, (a ten amino acid peptide) and two TMOF analogues were disclosed in U.S. Pat. Nos. 5,011,909 and 5,130,253, and in a 1990 publication (Borovsky, et al. [1990] FASEB J. 4:3015–3020). Additionally, U.S. Pat. No. 5,358,934 discloses truncated forms of the full length TMOF which have prolines removed from the carboxy terminus, including the peptides YDPAP (SEQ ID NO: 1), YDPAPP (SEQ ID NO: 1), YDPAPPP (SEQ ID NO: 1), and YDPAPPPP (SEQ ID NO: 1).

Neuropeptides Y (NPY) are an abundant family of peptides that are widely distributed in the central nervous system of vertebrates. NPY peptides have also been recently isolated and identified in a cestode, a turbellarian, and in terrestrial and marine molluscs (Maule et al., 1991 "Neuropeptide F: A Novel Parasitic Flatworm Regulatory Peptide from *Moniezia expansa* (Cestoda: Cyclophylidea)" Parasitology 102:309–316; Curry et al., 1992 "Neuropeptide F: Primary Structure from the Turbellarian, *Arthioposthia triangulata*" Comp. Biochem. Physiol. 101C:269–274; Leung et al., 1992 "The Primary Structure of Neuropeptide F (NPF) from the Garden Snail, *Helix aspersa*" Regul. Pep. 41:71–81; Rajpara et al., 1992 "Identification and Molecular Cloning of Neuropeptide Y Homolog that Produces Prolonged Inhibition in Aplysia Neurons" Neuron. 9:505–513).

Invertebrate NPYs are highly homologous to vertebrate NPYs. The major difference between vertebrate and invertebrate NPYs occurs at the C-terminus where the vertebrate NPY has an amidated tyrosine (Y) whereas invertebrates have an amidated phenylalanine (F). Because of this difference, the invertebrate peptides are referred to as NPF peptides.

Cytoimmunochemical analyses of NPY peptides suggest that they are concentrated in the brain of various insects, including the Colorado potato beetle *Leptinotarsa decemlineata* (Verhaert et al., 1985 "Distinct Localization of FMRFamide- and Bovine Pancreatic Polypeptide-Like Material in the Brain, Retrocerebral Complex and Subesophageal Ganglion of the Cockroach *Periplaneta americana*" L. Brain Res. 348:331–338; Veenstra et al., 1985 "Immunocytochemical Localization of Peptidergic Neurons and Neurosecretory Cells in the Neuro-Endocrine System of the Colorado Potato Beetle with Antisera to Vertebrate Regulatory Peptides" Histochemistry 82:9–18). Partial purification of NPY peptides in insects suggests that both NPY and NPF are synthesized in insects (Duve et al., 1981 "Isolation and Partial Characterization of Pancreatic Polypeptide-like Material in the Brain of the Blowfly alliphora vomitoria" Biochem. J. 197, 767–770).

Researchers have recently isolated two neuropeptides with NPF-like immunoreactivity from brain extracts of the Colorado potato beetle. The researchers purified the peptides using $C_{18}$ reversed phase high pressure liquid chromatography (HPLC), and determined their structure using mass spectrometry. The deduced structures of these peptides are: Ala-Arg-Gly-Pro-Gln-Leu-Arg-Leu-Arg-Phe-amide (SEQ ID NO. 1) and Ala-Pro-Ser-Arg-Leu-Arg-Phe-amide (SEQ ID NO. 2) designated NPF I and NPF II, respectively (Spittaels etal., 1996).

The present inventors have surprisingly discovered that NPF adversely affects TTLE biosynthesis in the midgut of female *Aedes aegypti* fed a blood meal and injected with NPF polypeptide. Because the structure of NPF is different from TMOF it appears that NPF does not bind to a TMOF-specific binding site on the gut receptor but to a different site on the same or different receptor. Furthermore, cytoimmunochemical analysis, by the inventors, of the mosquito gut after the blood meal, using antiserum against NPF, has surprisingly revealed that exocrine cells with NPF-like molecules that are synthesized by mosquito epithelial cells 24 hours after a blood meal. NPF therefore appears to be a secondary signal in a cascade of signals: first TMOF is released from the ovary, TMOF then binds to a TMOF gut receptor (Borovsky et al., 1994) that stimulates the synthesis and release of NPF from gut specific exocrine cells. NPF then binds to a receptor site on the gut at a site which may be adjacent to or part of the TMOF receptor, resulting cessation of biosynthesis of TTLE. This surprising discovery opens the door to a new generation of NPF pesticides, which inhibit biosynthesis of TTLE in a more direct manner than previously disclosed TMOF peptides.

2. BRIEF SUMMARY OF THE INVENTION

The present invention provides novel compositions comprising novel pesticidal compounds. The compounds are preferably polypeptides, such as peptides or proteins. In a preferred embodiment, these pesticidal compounds inhibit digestion in pests by inhibiting synthesis of pest digestive enzymes, such as TTLE. In a specific embodiment, these compounds can be used to control populations of pests, such as populations of blood-ingesting insects.

In one aspect, the compositions of the present invention comprise a pesticidal polypeptide which comprises an amino acid sequence having a formula:

$$A^1A^2A^3A^4A^5F^{LNK} \qquad \text{(Formula I)}$$

wherein:

$A^1$ is selected from the group consisting of Y, A, D, F, G, M, P, S and Y;

$A^2$ is selected from the group consisting of A, D, E, F, G, N, P, S and Y;

$A^3$ is optionally present and is selected from the group consisting of A, D, F, G, L, P, S and Y;

$A^4$ is optionally present when $A^3$ is present and is selected from the group consisting of A, F, G, L and Y;

$A^5$ is optionally present when $A^4$ is present and is selected from the group consisting of A, F, L and P;

$F^{LNK}$ is a flanking region which is optionally present and is selected from the group consisting of: P, PP, PPP, PPPP, and PPPPP;

The pesticidal polypeptide preferably does not consist of $YDPAP_6$, $DYPAP_6$, $PAP_6$, YDPAP, $YDPAP_2$, $YDPAP_3$, $YDPAP_4$, NPTNLH or DF-OMe.

In a narrower aspect the pesticidal polypeptide comprises an amino acid sequence which consists essentially of the amino acid sequence of Formula I. In a preferred aspect, the pesticidal polypeptide comprises a TMOF fragment TMOF amino acids adjacent to the amino acid sequence of Formula I. The fragment preferably has less than 50% of the number of amino acid residues of full-length native TMOF, preferably 2–5 amino acid residues. In still another aspect, the pesticidal polypeptide consists of the amino acid sequence of Formula I.

In another aspect, the present invention pertains to DNA sequences encoding the pesticidal polypeptides disclosed herein. Such DNA sequence can be used as known in the art to provide transformed plants or other food organisms which express a pesticidal polypeptide of the present invention.

The subject invention provides pest control compositions comprising pesticidal polypeptides formulated for application to the target pests or their situs. In a specific embodiment, prokaryotic or eukaryotic recombinant hosts which express a pesticidal polypeptide are provided by the subject invention. In a specific example, yeast or algae (preferably unicellular siliceous or green algae) are transformed to express a pesticidal polypeptide of the present invention. The transformed hosts can, for example, be applied to water areas where insect level such as mosquito larvae will ingest the transformed host, resulting in control of the mosquitoes by the pesticidal polypeptide. Furthermore, the polynucleotides of the present invention can be used to modify a virus, which may be used to deliver the polynucleotides to pest or other cells.

Another aspect of the present invention pertains to a method of controlling pests comprising administering to said pest or applying to a pest-inhabited locus an effective amount of a pesticidal polypeptide of the present invention.

The pesticidal polypeptides of the invention are also useful in controlling pest populations in areas of infestation, or areas susceptible to infestation and/or combating target pest populations, and can be employed along with pest repellents and pest attractants to control a pest population in a geographical area.

The invention also includes pesticidal compositions which contain one or more of the pesticidal polypeptides described above, including one or more of the pesticidal polypeptides and a pesticidally acceptable carrier, and also includes methods of killing or controlling insects which involve applying to the insects or their environment such pesticidal compositions. In one aspect, the pesticidal compositions of the present invention are administered in the form of a spray or a time release dosage unit. The pesticidal compositions can also comprise various other known pesticidal polypeptides or other pesticides targeting the same or different pests.

Methods of making pesticidal compositions are also included within the scope of the present invention which comprise bringing one or more of the said pesticidal polypeptides into association with a suitable carrier, diluent or excipient therefor.

As used herein, the term "pesticidally effective" is used to indicate an amount or concentration of a pesticide which is sufficient to reduce the number of pests in a geographical locus, as compared to a corresponding geographical locus in the absence of the amount or concentration of the pesticide.

The term "pesticidal" is not intended to refer only to the ability to kill pests, but also includes the ability to interfere with a pests life cycle in any way that results in an overall reduction in the pest population. For example, the term "pesticidal" included inhibition or elimination of reproductive ability of a pest, as well as inhibition of a pest from progressing from one form to a more mature form, e.g., transition between various larval instars or transition from larvae to pupa or pupa to adult. Further, the term pesticidal is intended to include all phases of a pest life cycle; thus, for example, the term includes larvicidal, ovicidal, and adulticidal action.

As used herein, the term "pest attracting" in reference to chemical or physical attractant (e.g., light attractant) means that the density of pests in an area in the presence of the attractant is greater than the density of pests in a corresponding area without the attractant. As used herein, the term "pest repelling" is correspondingly intended to indicate that the density of pests in an area in the presence of the repellent is lower than the density of pests in a corresponding area in the absence of the repellent.

The word "transform" is broadly used herein to refer to introduction of an exogenous polynucleotide sequence into a prokaryotic or eukaryotic cell by any means known in the art (including, for example, direct transmission of a polynucleotide sequence from a cell or virus particle as well as transmission by infective virus particles and transmission by any other known means for introducing a polynucleotide into a cell), resulting in a permanent or temporary alteration of genotype and in an immortal or non-immortal cell line.

The terms "peptide," "polypeptide," and "protein" as used herein are intended to refer to amino acid sequences of any length.

The term "pesticidal polypeptide" is used herein to indicate polypeptides comprising NPF and TMOF peptides, as well as fragments, derivatives and analogues and other functional equivalents of NPF and TMOF.

The methods and materials of the present invention provide a novel approach to controlling insects and insect-transmitted diseases. The peptides of the present invention have advantageous activity over previously disclosed compounds.

3. BRIEF DESCRIPTION OF THE DRAWINGS

FIG. 1 is a graph showing the inhibitory affect of NPF I on trypsin biosynthesis when injected into whole mosquitos. NPF I resulted in a 50% inhibition of trypsin biosynthesis when injected at a $1\times10^{-6}$ M concentration.

FIG. 2 is a graph showing the inhibitory affect of NPF II on trypsin biosynthesis when injected into whole mosquitos. NPF II resulted in a 35% inhibition of trypsin biosynthesis at a $1\times10^{-3}$ M concentration.

FIG. 3 is a graph showing the inhibitory affect of NPF I on trypsin biosynthesis when injected into ligated mosquito abdomens. NPF I resulted in a 54% inhibition of trypsin biosynthesis at a $1\times10^{-6}$ M concentration. These results strongly suggest that NPF acts on a receptor in the gut and not through a cell signaling transduction pathway which originates in the brain.

4. DETAILED DISCLOSURE OF THE INVENTION

The subject invention concerns novel pest control compounds and methods of use. For clarity of disclosure, and not by way of limitation, the detailed description of the invention is divided into the subsections which follow.

4.1 Pesticidal Polypeptides

The present invention provides novel compositions comprising novel pesticidal polypeptides and their use in controlling pests, such as mosquitoes.

One embodiment of the present invention concerns a pesticide composition comprising a polypeptide, wherein said polypeptide comprises an amino acid sequence having a formula:

$$A^1A^2A^3A^4A^5F^{LNK} \quad \text{(Formula I)}$$

wherein:

$A^1$ is selected from the group consisting of Y, A, D, F, G, M, P, S and Y;

A² is selected from the group consisting of A, D, E, F, G, N, P, S and Y;

A³ is optionally present and is selected from the group consisting of A, D, F, G, L, P, S and Y;

A⁴ is optionally present when A³ is present and is selected from the group consisting of A, F, G, L and Y;

A⁵ is optionally present when A⁴ is present and is selected from the group consisting of A,F,L and P;

$F^{LNK}$ is a flanking region which is optionally present and is selected from the group consisting of: P, PP, PPP, PPPP, and PPPPP;

The pesticidal polypeptide preferably does not consist of $YDPAP_6$, $DYPAP_6$, $PAP_6$, YDPAP, $YDPAP_2$, $YDPAP_3$, $YDPAP_4$, NPTNLH or DF-OMe.

In various embodiments, either $A^3A^4A^5$, $A^3A^4A^5F^{LNK}$, $A^4A^5$, $A^4A^5F^{LNK}$, $A^5$ or $A^5F^{LNK}$ are not present. Where $A^5$ is not present, $F^{LNK}$ may be attached directly to $A^4$. Where $A^4A5$ is not present, $F^{LNK}$ may be attached directly to $A^3$. Finally, where $A^3A^4A^5$ is not present, $F^{LNK}$ may be attached directly to $A^2$.

AAP (SEQ ID NO: 13), ADP (SEQ ID NO: 14), ADPAP (SEQ ID NO: 15), APA (SEQ ID NO: 16), DAA (SEQ ID NO: 17), DF (SEQ ID NO: 18), DPA (SEQ ID NO: 19), DY (SEQ ID NO: 20), DYP (SEQ ID NO: 21), FAP (SEQ ID NO: 22), FDP (SEQ ID NO: 23), FDPAP (SEQ ID NO: 24), FSP (SEQ ID NO: 25), $MPDYP_5$ (SEQ ID NO: 26), PAA (SEQ ID NO: 27), PAP (SEQ ID NO: 28), Y(D)DP (SEQ ID NO: 29), Y(D)DPAP (SEQ ID NO: 30), YAP (SEQ ID NO: 31), YD (SEQ ID NO: 32), YDA (SEQ ID NO: 33), YDAAP (SEQ ID NO: 34), YDF (SEQ ID NO: 35), YDFAP (SEQ ID NO: 36), YDG (SEQ ID NO: 37), YDLAP (SEQ ID NO: 38), YDP (SEQ ID NO: 39), (D)YDP (SEQ ID NO: 40), YDPAF (SEQ ID NO: 41), YDPAL (SEQ ID NO: 42), (D)YDPAP (SEQ ID NO: 43), YDPFP (SEQ ID NO: 44), YDPGP (SEQ ID NO: 45), YDPLP (SEQ ID NO: 46), YEPAP (SEQ ID NO: 47), YFPAP (SEQ ID NO: 48), YNPAP (SEQ ID NO: 49) and YSF (SEQ ID NO: 50), wherein "(D)" indicates that the amino acid residue in the chain is dextrorotary amino acid.

An alternative embodiment of the present invention comprises a pesticidal polypeptide having the formula:

$$A^1A^2 \quad \text{(Formula II)}$$

wherein

A¹ is an amino acid selected from the group consisting of A, D, F, M, and Y, and A² is an amino acid selected from the group consisting of A, D, E, P, and Y.

In a preferred embodiment, the subject invention is directed to peptides of Formula II wherein A¹ and A² are independently selected from the group consisting of A, D, and Y.

The peptides of the present invention are particularly advantageous because their smaller sizes permit more rapid and efficient penetration into the midgut. In addition, they are less expensive to produce by conventional chemical methods.

Also specifically exemplified herein as another embodiment are methods using an NPF polypeptide having the sequence Ala-Arg-Gly-Pro-Gln-Leu-Arg-Leu-Arg-Phe or Ala-Pro-Ser-Arg-Leu-Arg-Phe. The polypeptide is preferably amidated at the C-terminus, and may also be carboxylated at the N-terminus.

In a narrower aspect the pesticidal polypeptide comprises an amino acid sequence which consists essentially of the amino acid sequence of Formula I. In a preferred aspect, the pesticidal polypeptide comprises a TMOF or NPF fragment lacking TMOF or NPF amino acids adjacent to the amino acid sequence of the fragment. In still another aspect, the pesticidal polypeptide consists of the amino acid sequence of Formula I.

Preferably, the pesticidal polypeptides have an $LD_{50}$ against mosquito larvae of less than 3.0 moles/ml. More preferably, the peptides have an $LD_{50}$ of less than 2.0 moles/ml, and, most preferably, the peptides have an $LD_{50}$ of less than 1.0 moles/ml. As used herein, "$LD_{50}$" refers to a lethal dose of a pesticidal polypeptide able to cause 50% mortality of larvae maintained on a diet of 1 mg/ml autoclaved yeast. Borovsky and Mahmood (1995).

The pesticidal polypeptides of the present invention have advantageous biological activity against a wide variety of pests. They are particularly active against blood-sucking insects, particularly against blood-sucking insects of the order Diptera. In one aspect, the blood-sucking insects of the suborder Nematocera are preferred, especially the blood-sucking insects of the family Colicidae. In this aspect, blood-sucking insects of the subfamilies Culicinae, Corethrinae, Ceratopogonidae, and Simuliidae, are still more preferred, and those of the genera Culex, Theobaldia, Aedes, Anopheles, Aedes, Forciponiyia, Culicoides, and Helea are most preferred. Particularly preferred are various species of mosquitoes such as *Aedes aegypti* that are vectors of arthropodborne viral diseases and/or vectors of Plasmodium spp. These viruses may be, for example, arboviruses.

Other biting pests such as flies, fleas, ticks, grasshoppers and lice can also be controlled using peptides and methods of the present invention. These pests utilize serine esterases such as TTLE as their primary blood digesting enzymes. Thus, another class of insects which are preferred according to the present invention are those which employ serine esterases, as digestive enzymes. The subject peptides can also be used to control pests of agricultural crops. These pests include, for example, coleopterans (beetles), lepidopterans (caterpillars), and mites. The compounds of the present invention can also be used to control household pests including, but not limited to, ants and cockroaches.

A further aspect of the present invention are addition salts, complexes, or prodrugs such as esters of the pesticidal polypeptides, especially the pharmaceutically or agriculturally acceptable acid addition salts. The acid addition salts can be prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. Esterification to form derivatives such as the methyl or ethyl esters can be prepared by standard procedures.

The N-terminus and C-terminus of the peptides can be blocked to further inhibit proteolysis by metabolic enzymes. Derivation of peptides to block the N-terminus or C-terminus is known in the art. For example, the N-terminus can be acetylated by methods known to those of ordinary skill in the art; the C-terminus can be amidated as is well known in the art.

In a preferred embodiment of the invention, the pesticidal polypeptides may be presented as fusion proteins or peptides, the amino acid sequence of which includes one or more pesticidal polypeptides of the present invention. In various specific embodiments, two or more of the pesticidal polypeptides are linked, for example, by peptide bonds between the N-terminus of one portion and the C-terminus of another portion. In other aspects, one or more of the pesticidal polypeptides can be linked to one or more heterologous peptides or proteins to form pesticidal fusion peptides. Molecules comprising such portions linked by hydrocarbon linkages are also provided. Derivatives of the foregoing fusion proteins are also provided (e.g., branched, cyclized, N- or C-terminal chemically modified, etc.).

Polypeptides comprising the amino acid sequences of Formulas I and/or II in which only conservative substitutions have been made are also provided by the present invention. Analogs which have one or more amino acid substitutions forming a branched polypeptide (e.g., by substitution with an amino acid or amino acid analog having a free amino- or carboxy-side chain that forms a polypeptide bond with a sequence of one or more amino acids, including but not limited to prolines) or allowing circularization of the polypeptide (e.g., by substitution with a cysteine, or insertion of a cysteine at the amino- or carboxy-terminus or internally, to provide a sulfhydryl group for disulfide bond formation), are also provided.

Nonclassical amino acids or chemical amino acid analogs can be introduced as a substitution, added at a terminus or inserted between existing amino acid residues of the pesticidal polypeptides of the present invention. Non-classical amino acids include but are not limited to the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, C-methyl amino acids, N-methyl amino acids, and amino acid analogs in general. Furthermore, the amino acid can be D (dextrorotary) or L (levorotary). Dextrorotary amino acids are indicated herein by a parenthetical D, i.e., "(D)", immediately preceding the dextrorotary amino acid. The presence of D-conformation amino acids can inhibit the ability of proteases to degrade the peptides of the present invention.

Thus, the pesticidal polypeptide derivatives include peptides containing, as a primary amino acid sequence, all or part of the particular pesticidal polypeptide sequence including altered sequences in which functionally equivalent amino acid residues are substituted for residues within the sequence resulting in a polypeptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such pesticidal polypeptide derivatives can be made either by chemical synthesis or by recombinant production from a nucleic acid encoding the pesticidal polypeptide.

Also, derivation of these compounds with long chain hydrocarbons will facilitate passage through the cuticle into the pest body cavity. Therefore, a further embodiment of the present invention pertains to compositions comprising the peptides bound to lipids or other carriers.

The one-letter symbol for the amino acids used herein is well known in the art. For convenience, the relationship of the three-letter abbreviation and the one-letter symbol for amino acids is as follows:

| Arg | R | Lys | K |
|-----|---|-----|---|
| Asn | N | Met | M |
| Asp | D | Phe | F |
| Cys | C | Pro | P |
| Gln | Q | Ser | S |
| Glu | E | Thr | T |
| Gly | G | Trp | W |
| His | H | Tyr | Y |
| Ile | I | Val | V |

4.2 Preparation of Novel Pest Control Compounds
4.2.1 Synthetic Procedures

The novel pesticidal polypeptides of the invention can be prepared by well-known synthetic procedures. For example, the peptides can be prepared by the well-known Merrifield solid support method. See Merrifield (1963) *J. Amer. Chem. Soc.* 85:2149–2154 and Merrifield (1965) *Science* 150:178–185. This procedure, using many of the same chemical reactions and blocking groups of classical peptide synthesis, provides a growing peptide chain anchored by its carboxyl terminus to a solid support, usually cross-linked polystyrene or styrenedivinylbenzene copolymer. This method conveniently simplifies the number of procedural manipulations, since removal of the excess reagents at each step is effected simply by washing the polymer.

The pesticidal polypeptides can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y., pp. 34–49).

4.2.2 Recombinant Procedures

Alternatively, the pesticidal polypeptides can be prepared by use of well-known molecular biology procedures. DNA sequences encoding the peptides of the invention can be synthesized readily and are a further aspect of the present invention. These polynucleotides can be used to genetically engineer, for example, bacteria, insectcells, viruses, plant cells, fungi, algae, yeast, mammalian or other cells for synthesis of the peptides of the invention, as well as sythesis of fusion proteins or peptides comprising the peptides of the inventon.

One example of a cell line useful in accord with the teachings herein includes, the insect cell line Sf9 (*Spodoptera frugiperda*), deposit number ATCC CRL 1711, which is available from the American Type Culture Collection, 12301 Parklawn Drive, Rockville, Md. 20852 USA. An example of a useful virus includes Baculovirus *Autographa californica* nuclear polyhedrosis virus (AcNPV) which is available from Texas A&M University, Texas Agricultural Experiment Station, College Station, Tex. 77843, and has been described in Smith, G., M. D. Summers (1978) *Virology* 89:517–527; and (1979) *J. Virology* 30:828–838. Other nuclear polyhedrosis viruses (See World Health Organization Technical Report No. 531) such as *Spodoptera frugiperda* (*Sf* MNPV), *Choristoneura fumiferana* (*Cf* MNPV) (Smith, G., M. D. Summers [1981] *J. Virol.* 39:125–137), or *Spodoptera littoralis* (Sl NPV) (Harrap, K. A., C. C. Payne, J. S. Robertson [1977] *Virology* 79:14–31) can be used instead of *Autographa californica* NPV. Other insect cell lines can also be substituted for *Spodoptera frugiperda* (*Sf9*), for example, Trichoplusia ni (Volkman, L. E., M. D. Summers [1975] *J. Virol.*

16:1630–1637), *Spodoptera exigua*, *Choristoneura fumiferana* (Smith, G., M. D. Summers [1981] *J. Virol.* 39:125–137) and *Spodoptera littoralis* (Harrap, K. A. et al. [1977] *Virology* 79:14–31).

The present invention also provides polynucleotides encoding the subject pest pesticidal polypeptides. Polynucleotides can be produced by routine methods known in the art. See S. L. Beaucage and M. H. Caruthers (1981), *Tetrahedran Lett.* 22:1859.

If desired, the polynucleotide of the present invention can be amplified using PCR. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of Globin Genomic Sequences and Restriction Site Analysis for Diagnosis of Sickle Cell Anemia," *Science* 230:1350–1354.). PCR is based on the enzymatic amplification of a DNA fragment of interest that is flanked by two oligonucleotide primers that hybridize to opposite strands of the target sequence. The primers are oriented with the 3 ends pointing towards each other. Repeated cycles of heat denaturation of the template, annealing of the primers to their complementary sequences, and extension of the annealed primers with a DNA polymerase result in the amplification of the segment defined by the 5 ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated. Other enzymes which can be used are known to those skilled in the art.

PCR primers can be designed from the DNA sequences of the present invention. In performing PCR amplification, a certain degree of mismatch can be tolerated between primer and template. Therefore, mutations, deletions, and insertions (especially additions of nucleotides to the 5 end) of the exemplified sequences fall within the scope of the present invention. These PCR primers can be used to amplify genes of interest from a sample. Thus, this is another method by which polynucleotide sequences encoding the subject peptides can be readily identified and characterized.

The various methods employed in the preparation of plasmids and transformation of host organisms are well known in the art and are described, for example, in U.S. Pat. Nos. 5,011,909 and 5,130,253. These patents are incorporated herein by reference. These procedures are also described in Maniatis, T., E. F. Fritsch, J. Sambrook (1982) *Molecular Cloning: A Laboratory Manual*, Cold Spring Harbor Laboratory, New York. Thus, it is within the skill of those in the genetic engineering art to extract DNA from microbial cells, perform restrictions, enzyme digestions, electrophorese DNA fragments, tail and anneal plasmid and insert DNA, ligate DNA, transform cells (e.g., *E. coli*, or plant cells, fungal cells, algae cells, eukaryotic cells, etc.), prepare plasmid DNA, electrophorese proteins, and sequence DNA.

In one aspect the present invention is directed to a cell transformed with a polynucleotide encoding polypeptide compsising an NPF or TMOF polypeptide or a functional equivalent of an NPF or TMOF polypeptide, e.g., the TMOF polypeptides of Formulas 1 or 2.

Hosts which may be employed according to techniques well known in the art for the production of the polypeptides of the present invention include unicellular microorganisms such as prokaryotes, i.e., bacteria; and eukaryotes such as fungi, including yeasts, algae, protozoa, molds, and the like, as well as plant cells, both in culture or in planta, and animal cells and viruses. Particularly preferred in the case of mosquito targets are yeast and unicellular siliceous green algae. Specific bacteria which are susceptible to transformation include members of the Enterobacteriaceae, such as strains of *Escherichia coli*; Salmonella; Bacillaceae, such as *Bacillus subtilis*; Pseudomonas; Pneumococcus; Streptococcus; *Haemophilus influenzae*, and yeasts such as Saccharomyces, among others.

The polynucleotide sequences of the present invention can be introduced directly into the genome of the transformable host cell or can first be incorporated into a vector which is then introduced into the host. Exemplary methods of incorporation include transduction by recombinant phage or cosmids, transfection where specially treated host bacterial cells can be caused to take up naked phage chromosomes, and transformation by calcium precipitation. These methods are well known in the art. Exemplary vectors include plasmids, cosmids, and phages.

It is well known in the art that when synthesizing a gene for improved expression in a host cell it is desirable to design the gene such that its frequency of codon usage approaches the frequency of preferred codon usage of the host cell. For purposes of the present invention, "frequency of preferred codon usage" refers to the preference exhibited by a specific host cell in usage of nucieotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell.

Thus, in one embodiment of the present invention, bacteria, algae, fungi, plants, or other cells can be genetically engineered, e.g., transformed with polynucleotides encoding the subject peptides to attain desired expression levels of the subject peptides. To provide genes having enhanced expression, the DNA sequence of the gene can be modified to comprise codons preferred by highly expressed genes to attain an A+T content in nucleotide base composition which is substantially that found in the transformed host cell. It is also preferable to form an initiation sequence optimal for the host cell, and to eliminate sequences that cause destabilization, inappropriate polyadenylation, degradation and termination of RNA and to avoid sequences that constitute secondary structure hairpins and RNA splice sites. For example, in synthetic genes, the codons used to specify a given amino acid can be selected with regard to the distribution frequency of codon usage employed in highly expressed genes in the host cell to specify that amino acid. As is appreciated by those skilled in the art, the distribution frequency of codon usage utilized in the synthetic gene is a determinant of the level of expression.

Assembly of the polynucleotide sequences of this invention can be performed using standard technology known in the art. For example, a structural gene designed for enhanced expression in a host cell can be assembled within a DNA vector from chemically synthesized oligonucleotide duplex segments. Preferably, the DNA vector or construct has an operable promoter and suitable termination signals. The polynucleotide sequence can then be introduced into a host cell and expressed by means known in the art. Preferably, the peptide produced upon expression of the nucleotide sequence is functionally equivalent to the purified peptide. According to the subject invention, "functionally equivalent" refers to retention of function such as, for example, pest control activity.

The present invention also provides chimeric polypeptides comprising two or more pesticidal polypeptides of the present invention, or one or more polypeptides of the present invention with one or more heterologous polypeptides. The polypeptides which are combined need not themselves be pesticidal so long as the combination of portions creates a chimeric protein which is pesticidal. The chimeric polypeptides may include portions from polypeptides which do not necessarily act upon the TMOF receptor including, for example, toxins from *Bacillus thuringiensis* (*B.t.*). *B.t.* toxins and their various toxin domains are well known to those skilled in the art.

With the teachings provided herein, one skilled in the art can readily produce and use the various polypeptides and polynucleotide sequences described herein.

The polynucleotide sequences and pesticidal polypeptides useful according to the subject invention include not only the exemplified sequences but also fragments of these sequences, variants, mutants, and fusion proteins which retain the characteristic pesticidal activity of the peptides specifically exemplified herein. As used herein, the terms "variants" or "variations" of genes refer to nucleotide sequences which encode the same peptides or which encode equivalent peptides having pesticidal activity. As used herein, the term "functionally equivalent" in reference to polypeptides, refers to fragments, analogues, derivatives and other compounds which retain some or all biological activity against the target pests as the exemplified peptides.

Variations of genes may be readily constructed using standard techniques for making point mutations. Also, fragments of these genes can be made using commercially available exonucleases or endonucleases according to standard procedures. For example, enzymes such as Ba/31 or site-directed mutagenesis can be used to systematically cut off nucleotides from the ends of these genes. Also, genes which encode active fragments may be obtained using a variety of restriction enzymes. Proteases may be used to directly obtain active fragments of these peptides.

Polynucleotide sequences encoding the pesticidal polypeptides of the present invention can be introduced into a wide variety of microbial or plant hosts. Expression of the gene results, directly or indirectly, in the production and maintenance of the pesticide. With suitable microbial hosts (e.g., yeast, chlorella, etc.) the microbes can be applied to the situs of the pest, where they will proliferate and be ingested. The result is control or eradication of the pest. Alternatively, the microbe hosting the gene can be killed and treated under conditions that prolong the activity of the pesticidal polypeptide and stabilize the cell. The treated cell, which retains the toxic activity, then can be applied in a pesticidally effective amount to the environment of the target pest.

In one embodiment, the gene encoding the pesticidal polypeptide is only expressed or maintained by the transformed host for a relatively short period of time, such as days or weeks, so that the transformed organism does not continue indefinitely to express the pesticidal polypeptide. For example, in microbial hosts the plasmid may be constructed without plasmid maintenance systems or with insufficient plasmid maintenance function to ensure long-term survival of the pesticidal polypeptide-encoding plasmid. Alternatively, various plasmid maintenance systems known in the art can be applied either individually or together to ensure long-term survival of the pesticidal polypeptide-producing plasmid.

A wide variety of methods are available for introducing a polynucleotide sequence encoding a pesticidal polypeptide into a microorganism host under conditions which allow for stable maintenance and expression of the gene. These methods are well known to those skilled in the art and include, for example, the methods described in U.S. Pat. No. 5,135,867, which is incorporated herein by reference.

Synthetic genes encoding pesticidal polypeptides and/or functional equivalents thereof can also be used to transform hosts. Methods for the production of synthetic genes can be found in, for example, U.S. Pat. No. 5,380,831.

Recombinant cells expressing the pesticidal polypeptides of the present invention can be treated to prolong the pesticidal activity and stabilize the cell. For example, such cells can be treated to form a microcapsule comprising the pesticidal polypeptide within a stabilized cellular structure which protects the pesticidal polypeptide when the microcapsule is applied to the environment of the target pest. Suitable host cells include either prokaryotes or eukaryotes. Hosts of particular interest include the prokaryotes and the lower eukaryotes, such as algae and fungi. The cell is preferably intact and substantially in the proliferative form when treated, rather than in a spore form. Treatment of the microbial cell, e.g., a microbe containing the polynucleotide sequence encoding the pesticidal polypeptide, can be by chemical or physical means, or by a combination of chemical and/or physical means, so long as the technique does not completely diminish the properties of the pesticidal polypeptide nor diminish the cellular capability of protecting the pesticidal polypeptide. Methods for treatment of microbial cells are disclosed in U.S. Pat. Nos. 4,695,455 and 4,695,462, which are incorporated herein by reference.

4.3 Pesticidal Compositions and Methods of Administering Pesticidal Polyeptides and Compositions Control of pests using the pesticidal pesticides and compositions of the present invention can be accomplished by a variety of methods known to those skilled in the art.

4.3.1 Basic Pesticidal Formulations and Application Thereof

Amounts and locations for application of the pesticidal polypeptides and compositions of the present invention are generally determined by the habits of the insect pest, the lifecycle stage at which the pest is to be attacked, the site where the application is to be made and the physical and functional characteristics of the polypeptide.

The pesticidal polypeptides of the present invention are generally administered to the insect by oral ingestion, but may also be administered by means which permit penetration through the cuticle or penetration of the insect respiratory system. The pesticidal polypeptides may also be administered with other insect control chemicals, for example, the compositions of the invention may employ various chemicals designed to affect insect behavior, such as attractants and/or repellents as described in Sections 4.3.3.2 and 4.3.3.3, respectively, or as otherwise known in the art. The pesticidal polypeptides may also be administered with other insect control agents, such as chemosterilants.

Where the pesticidal polypeptides are formulated to be orally administered to the insect pests, the peptides can be administered alone or in association with an insect food. The peptides are preferably so associated with the food that it is not possible for the insect to feed on the food without ingesting the pesticidal polypeptide. Preferred foods for mosquito larvae are algae (particularly green, unicellular) and yeast. The food may comprise live organisms or killed organisms. In one embodiment for the control of plant pests, plants or other food organisms may be genetically transformed to express the pesticidal polypeptide such that a pest feeding upon the plant or other food organism will ingest the pesticidal polypeptide and thereby be controlled. The pesticidal polypeptide may also be mixed with an attractant to form a bait that will be sought out by the pest. Further, the pesticidal polypeptide may be applied as a systemic poison that is absorbed and distributed through the tissues of a plant or animal host, such that an insect feeding thereon will obtain an insecticidally effective dose of the pesticidal polypeptide.

The pesticidal polypeptides may also be formulated as contact pesticides which penetrate the insect cuticle or enter through the spiracles of the respiratory system. In one aspect, the pesticidal polypeptides of the present compound are formulated and applied as sprays, preferably using water as the principal carrier, although volatile oils may also be used.

The pesticidal polypeptides may be encapsulated, included in a granular form, solubilized in water or other appropriate solvent, powdered, and included in any appropriate formulation for direct application to the pest.

The pesticidal polypeptides may be used either alone or in combination with other active or inactive substances and may be applied by any method known in the art including, for example, spraying, pouring, dipping, in the form of concentrated liquids, solutions, suspensions, sprays, powders, pellets, briquettes, bricks and the like, formulated to deliver a pesticidally effective concentration of the pesticidal polypeptide. The pesticidal formulations may be applied in a pesticidally effective amount to an area of pest infestation or an area susceptible to infestation, a body of water or container, a barn, a carpet, pet bedding, an animal, clothing, skin, and the like.

For some applications the pesticidal polypeptides are bound to a solid support for application in powder form or in a "trap". As an example, for applications where the composition is to be used in a trap or as bait for a particular pest, the compositions of the present invention can be bound to a solid support or encapsulated in a time-release material. Examples of delivery systems include starch-dextran, and the like. See Yuan et al., Fundamental and Applied Toxicology (1993) 20: 83–87, for examples of delivery systems.

In all formulations described herein, materials which can lead to reduction in the pesticidal effectiveness of the peptides should be avoided but may be employed in appropriate circumstances where such materials do not entirely eliminate the pesticidal properties of the pesticidal polypeptide.

The pesticidal compositions may also include various pesticidally acceptable adjuvants known in the art. The term "adjuvant" is used herein to mean a substance added to a composition to aid the operation of the main ingredient. The adjuvants are pesticidally acceptable in that they do not completely diminish the pescidal properties of the pesticidal polypeptide. Spray adjuvants are commonly employed in the application of agricultural chemicals. An effective spray adjuvant may be formulated to contain one or more surfactants, solvents or co-solvents.

Formulated pesticidal polypeptides can also be applied as a seed-coating or root treatment or total plant treatment at later stages of the crop cycle. Plant and soil treatments may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal polypeptides according to the instant invention can be utilized, in the form of the usual compositions or compositions with conventional inert (e.g., plant and/or animal compatible or herbicidally mammacidally inert) pesticide diluents or extenders, i.e. diluents, carriers or extenders of the type usable in conventional pesticide compositions or compositions, e.g. conventional pesticide dispersible carrier vehicles such as gases, solutions, emulsions, suspensions, emulsifiable concentrates, spray powders, pastes, gels, soluble powders, dusting agents, granules, etc. These are prepared, for example, by extending the pesticidal polypeptides with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.); halogenated, especially chlorinated, aromatic hydrocarbons (e.g. chlorobenzenes, etc.); cycloalkanes (e.g. cyclohexane, etc.); paraffins (e.g. petroleum or mineral oil fractions); chlorinated aliphatic hydrocarbons (e.g. methylene chloride, chloroethylenes, etc.); alcohols (e.g. methanol, ethanol, propanol, butanol, glycol, etc.), as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as nonionic and/or anionic emulsifying agents (e.g. polyethylene oxide esters of fatty acids, polyethylene oxide ethers of fatty alcohols, alkyl sulfates, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc. The pesticidal polypeptides may also be encapsulated in a liposomal composition (Belles et al in Pesticide Biochem. Physiol. 32, 1–10 (1988)). Esters, such as succinate ester or citrate esters, can be employed to control the buoyancy of the composition.

The pesticidal polypeptides and compositions of the present invention can be delivered to the environment using a variety of devices known in the art of pesticide administration; particularly preferred devices are those which permit continuous extended or pulsed extended delivery of the pesticidal composition. For example, U.S. Pat. No. 5,417, 682 discloses a fluid-imbibing dispensing device for the immediate, or almost immediate, and extended delivery of an active agent over a prolonged period of time together with the initially delayed pulse delivery of an active agent to a fluid environment of use.

Other dispensing means useful for dispensing the pesticidal compositions of the present invention include, for example, osmotic dispensing devices which employ an expansion means to deliver an agent to an environment of use over a period of hours, weeks, days or months. The expansion means absorbs liquid, expands, and acts to drive out beneficial agent composition from the interior of the device in a controlled, usually constant manner. An osmotic expansion device can be used to controllably, usually relatively slowly and over a period of time, deliver the pesticidal compositions of the present invention. In one aspect, the invention provides a method for using such a device to deliver the pesticidal compositions of the present invention. In one aspect, the osmotic expansion device floats on water and delivers the pesticidal polypeptide to the surface of the water.

The compositions of the present invention may also be employed as time-release compositions, particularly for applications to animals, or areas that are subject to reinfestation, such as mosquito-infested ponds or animal quarters. Various time-release formulations are known in the art. Common analytical chemical techniques are used to determine and optimize the rate of release to ensure the delivery of a pesticidally effective concentration of the pesticidal polypeptide. The amount of the time-release composition necessary to achieve a pesticidally effective concentration of pesticide in the environment where the pesticide is applied, e.g., a body of water, is based on the rate of release of the time-release formulation. In one aspect, the time-release formulations may be formulated to float on top of the water. In another aspect, the formulation may be formulated to rest on the bottom, or below the surface of the body of water, and to gradually release small particles which themselves float to the surface, thereby delivering the pesticidal composition to the niche of the pest, e.g., mosquito larvae.

Delayed or continuous release can also be accomplished by coating the pesticidal polypeptides or a composition containing the pesticidal polypeptide(s) with a dissolvable or bioerodable coating layer, such as gelatin, which coating dissolves or erodes in the environment of use, such as in a pond, to then make the pesticidal polypeptide available, or by dispersing the peptides in a dissolvable or erodable matrix.

Such continuous release and/or dispensing means devices may be advantageously employed in a method of the present invention to consistently maintain a pesticidally effective concentration of one or more of the pesticidal polypeptides of the present invention in a specific pest habitat, such as a pond or other mosquito-producing body of water. In a preferred mode, the continuous release compositions are formulated by means known in the art, such that they can float on a body of water, thereby delivering the pesticidal polypeptide to the surface layer of the water inhabited by insect larvae.

In addition to providing bait or traps, infestations of target pests also can be treated using powder or detergent compositions, for example as a carpet shampoo. The compositions can also be used as emulsions or gels for treatment of infestations of animals or humans.

As would be appreciated by a person skilled in the art, the pesticidal concentration will vary widely depending upon the nature of the particular formulation, particularly whether it is a concentrate or to be used directly. The pesticide will be present in at least about 0.0001% by weight and may be 100% by weight. The dry formulations will have from about 1–95% by weight of the pesticide while the liquid formulations will generally be from about 0.0001–60% by weight of the solids in the liquid phase. The formulations that contain cells will generally have from about 1 to about $10^4$ cells/mg. These formulations will preferably be administered at about 50 mg (liquid or dry) to 1 kg or more per hectare.

4.3.2 Pesticidal Formulations Comprising Transformed Organisms and Application Thereof Where the polynucleotide sequence is introduced via a suitable vector into a microbial host, and said host is applied to the environment in a living state, it is preferred that certain host microbes be used. Microorganism hosts are preferably selected which are known to occupy the "phytosphere" (phylloplane, phyllosphere, rhizosphere, and/or rhizoplane) of one or more crops of interest or the situs where the pest proliferates and one preferably food organisms for the target pests. These microorganisms are preferably selected so as to be capable of successfully competing in the particular environment (e.g., crop, pond, marsh, or other insect habitats) with the wild-type organisms, provide for stable maintenance and expression of the gene expressing the polypeptide pesticide, and, desirably, provide for improved protection of the pesticide from environmental degradation and inactivation.

These methods include, for example, applying to the pests (or their locations) the recombinant microbes that have been transformed to express the pesticidal polypeptides, and/or providing the pesticidal polypeptides to the pests via plants transformed to express the pesticidal polypeptides of the present invention. Transformations can be made by those skilled in the art using techniques described herein or as otherwise known in the art.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter kylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. The pigmented microorganisms are particularly preferred.

Another mechanism by which the pesticidal polypeptides can be made available to pest species is through genetically engineering of food source organisms to produce the peptides. The food source organism will preferably be specific for the pest species, though this is not a necessity.

In applications to the environment of the target pest, a transformant strain, as described herein, expressing a pesticidal polypeptide according to the present invention, can be applied to the natural habitat of the pest. In some cases, transformant strain may grow in the habitat and/or in the pest upon ingestion, while producing the polypeptide(s) which will have a deleterious effect on the pest. However, the transformant strain may also be presented as a non-living organism. Such organisms may be applied by spraying, soaking, injection into the soil, seed coating, seedling coating or spraying, or the like. Where administered in the environment, concentrations of the organism will generally be from 0.0001 to $10^{10}$ cells/ml, and the volume applied per hectare will be generally from about 0.1 oz to 2 lbs or more. Where administered to a plant part inhabited by the target pest, the concentration of the organism will usually be from 0.0001 to $10^6$ cells/cm$^2$. The cells may also be administered as killed cells containing or associated with the pesticidal polypeptide.

Formulated bait granules containing an attractant and the pesticidal polypeptides, or recombinant microbes comprising pesticidal polypeptide-encoding polynucleotide sequences, can be applied to the pest habitat.

In aquatic environments, pest control may be attained at or below the surface by adjusting the specific gravity of the food organism. This can be done by, for example, varying the lipid content of the transformant microorganism strain. It is known that some indigenous aquatic algae float due to their lipid content. A variation in lipid content will allow the transformant strain to be distributed at desired depths below the water surface. Other organisms vary their buoyancy by varying their $CO_2$ content.

Preferred organisms for delivering the pesticidal polypeptide to mosquito larvae include various species of algae and yeast. Where algae is used, the algae is preferably green, unicelllular algae.

For commercial formulations, the organisms may be maintained in a nutrient medium which maintains selectivity and results in a low rate of proliferation. Various media may be used, such as yeast extract or L-broth. Once the organism is to be used in the field, the non-proliferating concentrate may be introduced into an appropriate selective nutrient medium, grown to high concentration, generally from about $10^9$ to $10^9$ cells/ml and may then be employed for introduction into the environment of the pest.

4.3.3 Methods for Controlling Insect Populations in a Geographical Locus

The pesticidal polypeptides and pesticidal compositions of the present invention may be used advantageously to control an insect population of a specific geographical area. The specific geographical area can be as large as a state or a county and is preferably ½ to 10 square miles, more preferably one square mile, and more preferably ½ to one square miles, and may also be much smaller, such as 100–200 square yards, or may simply include the environment surrounding and/or inside an ordinary building, such as a barn or house.

In general, the pesticidal polypeptides or compositions containing one or more of the pesticidal polypeptides are introduced to an area of infestation. For example, the composition can be sprayed on as a wet or dry composition on the surface of organic material infested with a target pest, or organic material or habitat susceptible to infestation with a target pest. Alternately, the composition can be applied wet or dry to an area of infestation where it can come into contact with the target pest. The pesticidal polypeptide or an organism which produces the pesticidal polypeptide may also be applied to an area of larvae development, for example, an agricultural area or a body of water such as a pond, rice paddy, watering hole or even a small puddle.

The methods of the present invention are carried out by exposing a target pest populatiori to a pesticidally effective amount of a pesticidal polypeptide and thereby decrease or eliminate the population of that pest in an area. The method of introduction of the pesticidal polypeptide into the target pest can be by direct ingestion by the target pest from a trap, or by feeding of a target pest on nutrient-providing organic matter treated with the pesticidal polypeptide, (e.g., killed yeast or algae in the case of mosquito larvae). In some instances, the pesticide may be absorbed by the pest, particularly where the composition provides for uptake by the outer tissues of the pest, particularly a larval or other pre-adult form of the pest, such as a detergent composition. For some applications it will be advantageous to deliver the pesticidal composition to the location of the pest colony. In other applications, it will be preferable to apply the pesticidal composition to a prey or host of the pest, such as a human or other animal.

The method of use of the pesticidal polypeptides and compositions will depend at least in part upon the pest to be treated and its feeding habits, as well as breeding and nesting habits.

The peptides according to the present invention may be employed alone or in mixtures with one another and/or with such solid and/or liquid dispersible carrier vehicles as described herein or as otherwise known in the art, and/or with other known compatible active agents, including, for example, insecticides, acaricides, rodenticides, fungicides, bactericides, nematocides, herbicides, fertilizers, growth-regulating agents, etc., if desired, in the form of particular dosage preparations for specific application made therefrom, such as solutions, emulsions, suspensions, powders, pastes, and granules as described herein or as otherwise known in the art which are thus ready for use. For example, a dosage form for a pond environment may be provided in the form of time releasable bricks, briquettes, pellets, powders, liquids, and the like, comprising at least one pesticidal polypeptide according to the present invention and at least one other active ingredient selected from the group consisting of insecticides, acaricides, rodenticides, fungicides, bactericides, nematocides, herbicides, fertilizers, and growth-regulating agents, for administration to the pond.

Various polypeptide fungicides useful in the methods and compositions of the present invention are disclosed in U.S. Pat. No. 5,872,152, entitled "Use of MMP inhibitors," issued to Brown, et al.; U.S. Pat. No. 5,861,478, entitled "Lytic peptides," issued to Jaynes, et al.; U.S. Pat. No. 5,804,588, entitled "Quinoline Carboxanides and their Therapeutic Use" issued to Dyke, et al.; U.S. Pat. No. 5,773,467, entitled "Benzofuran Sulphonamides," issued to Dyke, et al.; U.S. Pat. No. 5,773,413, entitled "Method of Combating Mammalian Neoplasias, and Lytic Peptides Therefor," issued to Jaynes, et al.; U.S. Pat. No. 5,744,445, entitled "Method of Treating Pulmonary Disease States With Non-Naturally Occuring Amphipathic Peptides," issued to Jaynes, et al.; U.S. Pat. No. 5,717,064, entitled "Methylated Lysine-Rich Lytic Peptides and Method Of Making Same by Reductive Alkylation," issued to Jaynes, et al.; U.S. Pat. No. 5,597,946, entitled "Method for Introduction of Disease and Pest Resistance Into Plants and Novel Genes Incorporated Into Plants Which Code Therefor," issued to Jaynes, et al.; and U.S. Pat.

No. 5,597,945, entitled "Plants Genetically Enhanced for Disease Resistance," issued to Jaynes, et al.

4.3.3.1 Methods Comprising Application of Other Pesticides

The peptides of the present invention may be beneficially administered in conjunction with other active ingredients (sequentially or simultaneously), including other pesticides, as well as various acaricides, algicides, antioxidants, antipreservatives, bactericides, biocides, catalysts, chemical reactants, disinfectants, drugs, fermentation agents, fertility inhibitors, fertility promoters, fertilizers, food supplements, foods, fungicides, germicides, growth-regulating agents, herbicides, insecticides, microorganism attenuators, nematocides, plant growth inhibitors, plant growth promoters, preservatives, rodenticides, sex sterilants, and sterilization agents, and/or other agents that benefit the environment of use. For simultaneous administration, the active ingredients may be formulated into a unitary application form comprising at least one pesticidal polypeptide and one or more of such active ingredients.

Insecticides may be classified by the chemical nature and source of supply as inorganic compounds, organic compounds of plant origin, and synthetic organic compounds. Organic insecticides are generally active only as stomach poisons, while plant derivatives act largely as contact poisons, and synthetic organic insecticides may have contact and stomach action and are sometimes used as fumigants.

The compositions of the present invention may comprise various inorganic stomach poisons, such as arsenicals, fluorides, etc. various arsenicals have been widely used as stomach poisons for insects. Arsenicals which may be employed in compositions of the present invention may include, for example, arsenous oxides such as arsenic trioxide; arsenites (trivalent) such as sodium arsenite; arsenates such as lead arsenate, calcium arsenate, copper arsenate, etc. Fluorides which may be employed in compositions of the present invention include, for example, sodium fluoride, sodium fluorosilicate, barium fluorosilicate, sodium fluoroaluminate, etc. Other inorganic insecticides which may be employed in compositions of the present invention include, for example, borax ($Na_2B_4O_7 \cdot 10H_2O$), sodium tetraborate, glyceroboric acid, mercuric chloride, mercurous chloride, cuprous cyanide, zinc phosphide, thallium sulfate, sodium selenate, white phosphorus, silicic acid, elemental sulfur, lime sulfur (a water-soluble mixture of calcium pentasulfide, calcium tetrasulfide, calcium thiosulfate, and calcium sulfite), etc.

The compositions of the present invention may also include various contact poisons of plant origin, such as nicotinoids, e.g., nicotine, nornicotine, and anabasine; pyrethroids such as pyrethrin I and II, cinerin I & II and jasmolin I & II, and rotenoids. Rotenoids include rotenone, as well as other naturally-occurring rotenoids such as elliptone, sumatrol, malaccol, degueline.

The compositions and methods of the present invention may also employ various forms of Sabadilla, including, for example, cevadine, vatridine, cevadilline and sabadine.

The compositions and methods of the present invention may also employ various forms of Ryania, such as ryanodine.

The compositions and methods of the present invention may also employ various synthetic organic insecticides. One class of synthetic organic insecticides includes Dinitrophenols, such as dinitrocresol. The compounds include various derivatives of 4,6-dinitro-2-alkylphenols and of their salts or esters. Other dinitrophenols include, for example, dinoseb, 4,6-dinitro-2-sec-butylphenol, binapacryl, 3-methyl-2-butenoate ester, dinocap, and 2-(6-methylheptyl)-4,6-dinitrophenyl crotonate.

Another class of synthetic organic insecticides includes organothiocyanates, such as 2-(2-butoxylethoxy)ethyl thiocyanate and DDT. Another class of synthetic organic insecticides useful according to the present invention includes analogues of DDT. Several closely related compounds have attained commercial importance as insecticides, such as DDD, 1,1-chloro-2,2-bis-(p-chlorophenyl)ethane, and methoxyclhor, 1,1,1-trichlor-2,2-bis-(p-methoxyphenyl) ethane.

Other synthetic organic insecticides useful according to the present invention are benzene hexachloride and lindane. Chlorinated Terpenes such as toxaphene, cyclodienes, chlordene, telodrin, aldrin, endrin, endosulfan, mirex, and chlordecone are also useful in the methods and compositions of the present invention.

Other synthetic organic insecticides useful according to the present invention include organophosphorus insecticides such as tetraethyl pyrophosphate (TEEP), mevinphos, parathion, azinphosmethyl, malathion, schradan, demeton, dimethoate, phorate, disulfoton, trichlorfon, sulfotepp (tetraethyl dithionopyrophosphate), methyl parathion, dicapthon, fenthion, ronnel, bromophos, fenitrothion, chlorpyrifos, temephos, diazinon, azinphos, dioxathion, EPN, (o-ethyl o-p-nitrophenyl phenylphosphonothionate), phosmet, dialifor, carbophenothion, chlorfenvinphos, methamidophos, prophos, ethion, demeton methyl, phosphamidon, dicrotophos, morphothion, crufomate, and crotoxyphos.

The Carbamates are another class of synthetic organic insecticides useful in the compositions and methods according to the present invention. Carbamates are synthetic relatives of the alkaloid physostigmine from *Physostigma venenosum* and include, for example, carbaryl, carbofuran, propoxur, dioxacarb, bendiocarb, aldicarb, methomyl, oxamyl, pyrimicarb, dimetilan, mexacarbate, methiocarb, formetanate, metalkamate, and promecarb.

Synthetic pyrethroids, such as allethrin, repsent still another class of synthetic organic insecticides useful in the compositions and methods according to the present invention. Also useful are pyrethroids from chrysanthemic acid, such as barthrin and resmethrin. Dimethrin has outstanding mammalian safety and has been used as a mosquito larvicide that is safe for use in potable waters, e.g., rain barrels and cisterns.

Another class of synthetic organic insecticides useful in the compositions and methods according to the present invention includes pyrethroids with modified acid components, such as permethrin, decamethrin, and fenvalerate.

Another class of synthetic organic insecticides useful in the compositions and methods according to the present invention includes insect growth regulators such as neurotoxins and acetylcholinesterase. The insect growth regulators that interfere with biochemical and physiological processes that are highly unique to the arthropods, e.g., molting, ecdysis and formation of the chitinous exoskeleton.

Another class of synthetic organic insecticides useful in the practice of the present invention includes Juvenoids such as neotenin, neotenin analogues, neotenin, r-20458, hydroprene, and methoprene.

Also useful in the practice of the present invention is the class of synthetic organic insecticides which includes chitin syntheses inhibitors such as diflubenzuron. One member of this class, Methoprene™, has seen effective commercial usage as a mosquito larvicide and for horn-fly control (when fed to cattle) in manure.

Other classes of synthetic organic insecticides useful in the practice of the present invention include acaricides, and fumigants such as acrylonitrile, carbon disulfide, carbon tetrachloride, chloropicrin, 1,2-dibromo-3-chloro-propane, β,β'-dichlorodiethyl ether, 1,1-dichloro-1-nitroethane, 1,2-dichloropropane trans-1,3-dichloropropene, ethylene chlorobromide, ethylene dibromide, ethylene dichloride, ethyl formate, ethylene oxide, hydrogen cyanide, β-methallyl chloride, methyl bromide, methyl formate, naphthalene, p-dichlorobenzens, phosphine, sulfuryl fluoride, trichloroacetonitrile and trichloroethylene.

The compositions and methods of the present invention may also include various insecticides from microbial sources. Insects are attacked by a multitude of pathogens and ca. 450 viruses, 80 bacteria, 460 fungi, 250 protozoa, and 20 rickettsial disease are effective natural enemies and are adaptable for mechanical dissemination as microbial insecticides for the inoculation of insect populations, soils, fields, orchards or forests with spores, microbial toxins or virus suspensions. Examples include *Bacillus popillae* spores and spores of *Bacillus thuringiensis* (*B.t.*). Preferred strains of *B.t.* include, for example, *B.t. israeliensis, B.t. tenebrionis, B.t. san diego, B.t. aizawai, B.t. subtoxicus, B.t. alesti, B.t. gallaeriae, B.t. sotto, B.t. kurstaki, B.t. berliner, B.t. tolworthi, B.t. dendrolimus* and *B.t. thuringiensis*, and various delta-endotoxins, as described, for example, in U.S. Pat. No. 5,686,069. Furthermore, *Bacillus sphaericus* is highly specific for control of mosquito larvae.

The methods and compositions of the present invention may also usefully employ a variety of insect viruses known in the art to cause epizootics in insect populations, and may also employ fungal spores of *Beauveria bassiana*

In one aspect the compositions and/or methods of the present inventon comprise and/or employ a pesticidally effective combination of one or more pesticidal polypeptides of the present invention and one or more pesticides selected from the group consisting of: acephate, acrylonitrile, aldicarb, aldrin, allethrin, alphamethrin, amitraz, azamethiphos, azinphos-ethyl, azinphos-methyl, bendiocarb, bromophos, bromophos-ethyl, bufencarb, buprofezin, butocarboxim, butoxycarboxim, calcium arsenate, camphechlor, carbaryl, carbofuran, carbophenothion, carbosulfan, chlordane, chlordecone, chlordimeform, chlorfenvinphos, chlormephos, chloropicrin, chlorpyrifos, chlorpyrifos-methyl, chlorthion, chlorthiophos, crotoxyphos, cypermethrin, DDT, deltamethrin, demeton, demeton-S-methyl, demeton-S-methyl sulphone, dialifor, diazinon, dichlofenthion, dichlorvos, dicrotophos, dieldrin, diflubenzuron, dimefox, dimethoate, dimetilan, dinex, dinoseb, dioxacarb, dioxathion, disulfoton, DNOC, endosulfan, endrin, ethiofencarb, ethion, ethoprophos, ethylene dibromide, ethylene oxide, etrimfos, fenazox, fenchlorphos, fenitrothion, fenoxycarb, fenpropathrin, fensulfothion, fenthion, fenvalerate, flucythrinate, fluvalinate, fonofos, formetanate, formothion, furathiocarb, heptachlor, heptenophos, hydrogen cyanide, iodofenphos, isofenphos, kadethrin, kelevan, kinoprene, lindane, malathion, mephosfolan, mercaptodimethur; metham-sodium, methamidophos, methidathion, methomyl, methoprene, methoxychlor, methyl bromide, methyl isothiocyanate, mevinphos, monocrotophos, naled, nicotine, omethoate, oxamyl, oxydemeton-methyl, parathion, parathion-methyl, permethrin, perthane, petroleum oil, phenthoate, phorate, phosalone, phosmet, phosphamidon, phosphine, phoxim, pirimicarb, pirimiphos-methyl, plifenate, promecarb, propetamphos, propoxur, prothiofos, prothoate, pyrethrins, quinalphos, resmethrin, rotenone, sulfotepp, sulprofos, tar oil, temephos, terbufos, tetrachlorvinphos, tetramethrin, thiocyclam hydrogen oxalate, thiofanox, thiometon, thionazin, triamiphos, triazophos, trichlorfon, trichloronat and vamidothion.

As already mentioned, the pesticides of the present invention may be beneficially administered with other pesticides either together in a single composition with the pesticidal polypeptides of the present invention, or separately (simultaneously or sequentially), for example, as part of an integrated pest management approach which also employs various methods and substances known to promote the vitality of natural pest enemies, such as parasites, predators and/or microbes which are pathogenic to the target pests.

U.S. Pat. No. 5,839,224 teaches the use of natural aromatic compounds for use as pesticides and which can be included in the pesticidal methods and compositions of the present invention, including, for example, cinnamic aldehyde, coniferyl aldehyde, cinnamic acid, cinnamic ester and closely related compounds. Exemplary compounds include 2-(phenylmethylene) octanal, benzaldehyde, acetaldehyde, cinnamaldehyde, piperonal, and vanillin. Other compositions including cinnamic aldehyde and its derivatives are disclosed in U.S. Pat. No. 4,978,686, French Patent Application No. 2529755, U.S. Pat. No. 2,465,854 and U.S. Pat. No. 5,639,794.

Furthermore, the compositions of the present invention may also include various pesticidal neuropeptides known in the art. For example, U.S. Pat. No. 5,863,763 describes neuropeptides isolated and purified from the blowfly *Calliphora vomitoria* that have been designated callatostatins.

Additionally, the methods and pesticidal compositions of the present invention may include pesticidal N-carboxylated N-methylcarbamic acid aryl esters as described in U.S. Pat. No. 4,014,923, which are also known to possess pesticidal properties. Examples of N-carboxylated N-methylcarbamic acid aryl esters which may be usefully employed in pesticidal compositions of the present invention include, for example, N-(phenoxycarbonyl)-N-methylcarbamic acid phenyl ester, 2-isopropoxyphenyl ester, 3,5-dimethyl-4-methylmercaptophenyl ester, 3-methyl-4-dimethylaminophenyl ester, 2-cyclopentylphenyl ester, 2-dioxolanylphenyl ester, 2-chlorophenyl ester, 4-tolyl ester, 2-methoxy-4-methylphenyl ester, 4-trifluoromethylphenyl ester, 4-nitrophenyl ester, 2-allyloxyphenyl ester, 4-propargylphenyl ester, 1-naphthyl ester, 7-(2,2-dimethyl-2,3-dihydrobenzofuranyl) ester, 3-dimethylformamidinophenyl ester, methyl ester, isopropyl ester, sec. butyl ester, methallyl ester, propargyl ester, amide, dimethylamide, allylamide, dodecylamide, cyclohexylamide, anilide, 4-chloroanilide, 3-nitroanilide, 4-aniside, morpholide and 2-pyridylamide; N-(2-isopropoxyphenylcarbonyl)-N-methylcarbamic acid 2-isopropoxyphenyl ester, 3,5-dimethyl-4-methylmercaptophenyl ester, 2-cyclopentylphenyl ester, thiomethyl ester, thiobutyl ester, thiophonyl ester, 4-chlorothiophenyl ester, dimethylamide, allyl ester, 2-chloroethyl ester, 2-methoxyethyl ester, 2-diethylaminoethyl ester and 2-ethylmercaptoethyl ester; N-(3-methyl-4-dimethylaminophenoxycarbonyl)-N-methylcarbamic acid 2-chlorophenyl ester, 2-dioxolanylphenyl ester, 2-isopropylphenyl ester, methylamide, diallylamide, cyclopentyl ester, benzyl ester and 4-nitrobenzyl ester; N-(1-naphthoxycarbonyl)-N-methylcarbamic acid 2-methoxyphenyl ester, ethyl ester, propargyl ester and isopropyl ester; N-(7-(2,2-dimethyl-2,3-dihydrobenzofuranoxy))-N-methylcarbamic acid 2-dioxolanylphenyl ester, butyl ester, isopropylamide, thioethyl ester, and thio-4-methylphenyl ester.

Further, the pesticidal methods and compositions of the present invention may include various ovicidal ingredients. For example, U.S. Pat. No. 3,719,763 describes a binary aqueous spray ovicidal composition useful in controlling *Aedes aegypti* including apolar amine (e.g., decylamine) and a polar amine (e.g., ethanolamine).

Other pesticides useful in the compositions of the present invention include the biodegradable pesticides described in U.S. Pat. 5,270,345.

Further, the pesticidal methods and compositions of the present invention may advantageously include polychlorinated cyclic hydrocarbons that have been known for many years as good insecticides. Such insecticides as DDT, dieldrin, endrin, chlordane, lindane, heptaclor, aldrin, and toxaphene are examples. While many of these insecticides are generally environmentally unacceptable due to, their lack of specificity and tendency to bioaccumulate, they may find use in environmentally compatible lower doses in compositions employing the pesticidal polypeptides of the present invention.

Another pesticide useful in the compositions of the present invention is Pyrethrum, a powerful, rapidly acting insecticide originally derived from the crushed and dried flowers of the daisy *Chrysanthemum cinerariifolium*.

The methods of the present invention also employ manipulation of the mechanisms of inheritance of the insect pest populations, for example by mass release of sterilized males, environmental use of chemosterilants, and the mass introduction of deleterious mutations, e.g., conditional lethals and chromosomal translocations. For example, the methods of the present invention include the use of such methods while simultaneously or consecutively attacking the insect population using the insecticidal compositions of the present invention.

The release of large numbers of sterile male insects into a population of virgin females has been shown to reduce the number of fertile females in subsequent generations.

The present invention may also employ various chemicals that sterilize natural segments of natural insect pest populations. Several types of chemosterilants are known to produce adequate sterility in insects by preventing the production of ova or sperm, by causing death of sperm or ova, or by producing severe injury to the genetic material of sperm or ova so that the zygotes that are produced do not develop into mature progeny. Further, antimetabolites such as 5-fluorouracil and amethopterin, a folic acid antagonist, which produce sterility in female flies when fed at 0.01–0.05% in the diet, may be employed.

Radiomimetic compounds which include cancer chemotherapeutic compounds that incorporate the extremely reactive ethyleneimine group may also be employed, such as tepa or 1-tris(1-aziridinyl)-phosphine oxide and its thionoanalogue, thiotepa. These compounds are alkylating agents for DNA and cause sterility in both sexes of the housefly, e.g., when incorporated into food or applied topically. Other similar radiomimetic compounds include apholate or 2,2,4,4,6,6-hexa-(1-aziridinyl)-2,4,5-triphospho-1,3,5-triazine and hempa or hexamethyltriphosphoramide.

While many such compounds, including hempa, are mutagens and strong carcinogens, and while their casual and indiscriminate use in insect control is therefore precluded, they may be administered using methods and in circumstances in which human contact is minimized or avoided.

4.3.3.2 Methods Comprising Application of Attractants

The methods and compositions of the present invention also comprise and/or include the use of various pest attractants known in the art.

Various attractants are known which influence pest behavior as pests search for food, oviposition sites, or mates. Many of these chemicals are used to attract insect pests into traps or to poison baits both for population control and for measurement of population densities, e.g., for timing spray applications. Attractants useful in the methods and compositions of the present invention include, for example, eugenol, phenethyl propionate, ethyl dimethylisobutyl-cyclopropane carboxylate, propyl benszodioxancarboxylate, cis-7,8-epoxy-2-methyloctadecane, trans-8,trans-0-dodecadienol, cis-9-tetradecenal (with cis-11-hexadecenal), trans-11-tetradecenal, cis-11-hexadecenal, (Z)-11,12-hexadecadienal, cis-7-dodecenyl acetate, cis-8-dodecenyul acetate, cis-9-dodecenyl acetate, cis-9-tetradecenyl acetate, cis-11-tetradecenyl acetate, trans-11-tetradecenyl acetate (with cis-11), cis-9,trans-11-tetradecadienyl acetate (with cis-9,trans-12), cis-9,trans-1 2-tetradecadienyl acetate, cis-7,cis-11- hexadecadienyl acetate (with cis-7,trans-11), cis-3,cis-13-octadecadienyl acetate, trans-3,cis-13-octadecadienyl acetate, anethole and isoamyl salicylate. Other attractants which may be employed according to the methods and compositions of the present invention are described in U.S. Pat. No. 4,816,248, which describes the use of the ethyl ester of 2-methyl-3-pentenoic acid as mosquito attractants. The insect attractants may be presented as insect attractant-containing polymer particles as described in U.S. Pat. No. 5,683,687.

Carbon dioxide and 1-octen-3-ol (octenol) are also known as mosquito attractants. U.S. Pat. No. 4,902,504 describes the use of dibutyl succinate, dimethyl disulfide and mixtures thereof as mosquito attractants.

The present invention may also employ various sex pheromones as insect attractants. Sex pheromones are distributed widely throughout the Insecta and are specific chemicals or mixtures of chemicals generally secreted by glands in the terminal segments of the female abdomen, which attract males upwind from long distances.

The time-release dosage units of the present invention preferably contain a chemoattractant or other attractant to attract the insect or larva to the vicinity of the dosage unit where the concentration of the pesticidal polypeptide will necessarily be greatest. Attractants are substances that lure insects through olfactory stimulation, such as food lures, sex lures, or oviposition lures. Suitable insect attractants are as described herein or as otherwise known in the art, and include, for example, lavender absolute (U.S. Pat. No. 5,683,687). Further attractants having utility according to the methods and compositions described herein are described in U.S. Pat. No. 5,464,626 which teaches dimethyl substituted oxymethyl cyclohexane derivatives having utility as repellents or attractants against or for various insect species, including *Aedes aegypti, Aedes vexans, Aedes infirmatus* and others.

Means other than chemoattractants may also be used to attract insects, according to the present invention. For example, various insects, including mosquitoes, are attracted by light, the color blue and heat. Members of various species of mosquitoes are attracted to light in various wavelengths. Some species of mosquitoes are attracted to light in a range of ultraviolet (UV) wavelengths, and certain infrared wavelengths. Fluorescent lights with special phosphors to enhance the ultraviolet spectral content of the emitted light may be used as the light source.

4.3.3.3 Methods Comprising Application of Repellents

The methods and compositions of the present invention can also be used in population control in conjunction with a wide variety of repellents commonly known in the art.

Repellents are substances that protect animals, plants or products form insect attack by making food or living conditions unattractive or offensive.

For example, creosote lines can be used as barriers to the migration of chinch bugs; trichlorobenzene and other chemicals can be used to protect buildings from termites; heavy oils at the base of poultry roosts serve as a barrier to poultry mires; and various chemical bands can be employed about tree trunks.

Repellents against the feeding of insects include, for example, the application of bordeaux, lime and similar washes to plants to ward off leafhoppers and some chewing insects; mosquito repellents and fly sprays to lessen the attacks of blood-sucking flies and mosquitoes; the application of sulfur to the body to keep chiggers from attacking; the use of smoke and smudges to repel biting flies; the chemical treatment of logs to keep beetle borers from destroying log cabins and other rustic work; and moth balls, oil of cedar, and mothproofing treatments to protect materials from attack by clothes moths and carpet beetles.

Repellents against the egg laying of insects include, for example, the use of pine-tar oil and diphenylamine to keep screwworm flies from laying eggs about wounds of animals.

Bordeaux mixture is repellent to many insects. It is, to some extent, an ovicide and has some residual toxic effect upon the sap and, thereby, kills leafhoppers and psyllids. Bordeaux mixture is produced by mixing hydrated lime, 3.6–4.5 kg (8–10 lb), and copper sulfate, 1.0–2.7 kg (4–6 lb), in 380 L (100 gal) of cold water to produce a precipitate of tetracupric sulfate, $4CuO.SO_3$. Other repellents useful in the methods of the present invention include: thiram or tetramethylthiuram disulfide, nabam, and disodium ethylenebisdithiocarbamate, and 4'-(dimethyltriazeno) acetanilide.

Preferred repellents against bloodsucking insects will provide effective protection of the treated area for several hours, will work on all types of target pests, and under all climatic conditions; will be non-toxic and will not cause irritation when regularly applied to human or animal skin; will be cosmetically acceptable, will be free from unpleasant odor, taste, and touch, and harmlessness to clothing; will protect against a wide variety of biting insects; and will be available at low cost.

Other repellents used according to the present invention include, for example, brenzil, benzyl benzoate, 2,3,4,5-bis (butyl-2-ene)-tetrahydrofurfural, butoxypolypropylene glycol, N-butylacetanilide, n-butyl 6,6-dimethyl-5,6-dihydro-1,4-pyrone-2-carboxylate, dibutyl adipate, dibutyl phthalate, di-n-butyl succinate, N,N-diethyl-m-toluamide, dimethyl carbate (cis-dimethyl bicyclo[2,2,1]-5-heptene-2, 3-dicarboxylate), dimethyl phthalate, 2-ethyl-2-butyl-1,3-propanediol, 2-ethyl-1,3-hexanediol, di-n-propyl isocinchomeronate, 2-phenylcyclohexanol, n-propyl N,N-diethylsuccinamate.

In a method aspect of the present invention, specific geographical areas populated by humans or livestock can be treated with an insect repellent, and unpopulated areas where insect larvae (e.g., mosquito larvae) grow and breed can be treated with a pesticidal polypeptide or composition of the present invention, preferably in conjunction with an attractant, such that pests are repelled from the populated area and attracted to the pesticidal composition. The repellent can be applied, for example, to a surface, such as the skin of an animal (e.g., livestock or human), clothing, bark, plant parts, habitat components and the like, from which it is desirable to repel insects and other pests. For animal targets, repellents may be applied directly to the animal while the compositions of the present invention are located away from the animal and its habitat, preferably with an attractant either within the pesticidal composition itself or near the composition such that pests are both repelled from the animal host and attracted to the pesticidal composition. The distance between the attractant and repellent will depend on the specific pest, the specific attractant and the specific repellent, and is readily ascertainable by one of skill in the art. For highly mobile pests, such as mosquitoes, the attractant and repellent will preferably be located large distances apart, such as hundreds of meters apart. In other circumstances, the attractant and repellent may be located within the same building, such as in a barn. Furthermore, it will be appreciated by those of skill in the art that the repellent may also be located near or formulated with the pesticidal polypeptides of the instant invention, particularly where the repellent is only partially effective.

Examples of repellents which may be used according to the methods present invention include, for example, DEET (N,N-diethyl-1,3-methylbenzamide), carbon dioxide, citronella (the active ingredient most commonly found in "natural" or "herbal" insect repellents marketed in the United States) and Bite Blocker (Consep, Inc., Bend, Oregon), a plant-based repellent that was released in the United States in 1997. Bite Blocker combines soybean oil, geranium oil, and coconut oil. Further, U.S. Pat. No. 5,093, 326 discloses repellent compositions that include an ozonized unsaturated hydrocarbons, including terpenes. Publications relating to repellent compositions include Reifenrath et al. (1989) J. Am. Mosquito Control Association 5: 45–61 and Reifenrath (1995) Cosmetics & Toiletries Magazine 110: 85–93, SE 8900902, BR 9203522, JP 57126401, JP 3127702, JP 1261303, JP 5178712, JP 3268901, JP 3007554, JP 57040402, J. Chem. Ecol. (1990) 16:8: 2401–2428, DE 3605753, JP 5139924, JP 4176460, FR 2529755, JP 57120501, a JP 1261303.

4.3.3.4 Methods Comprising Traps

The methods of the present invention may also employ various pest traps known in the art, such as the ZOECONTM sticky trap. Various insect traps useful in the methods of the present invention are disclosed in U.S. Pat. Nos. 5,749,168, 5,67,576 and 5,647,164.

U.S. Pat. No. 3,120,075 describes a mosquito trap which comprises a light source suspended above a container into which is suspended a jar containing insecticide for killing the insects. According to the present invention, the pesticide may comprise a pesticidal polypeptide or composition thereof as described herein. A propeller disposed at the other end of the container creates a draught to cause the mosquitoes to fall into the "killing" jar. Other devices are described in U.S. Pat. No. 5,255,468 to Cheshire, which describes an insect attracting and capturing apparatus for capturing and killing mosquitoes, and in U.S. Pat. Nos. 2,806,321, 3,041, 773, 3,152,420, 4,908,978, 4,238,878, and 5,799,436.

All of the U.S. patents and other references cited herein are hereby incorporated herein in their entireties.

5. EXAMPLES

The following are examples illustrate procedures for practicing the invention. These examples should not be construed as limiting. All percentages are by weight and all solvent mixture proportions are by volume unless otherwise noted.

5.1 Effect of TMOF Analogs on Mosquito Larvae

TMOF can traverse the gut epithelium, enter the hemolymph and bind a gut receptor (Borovsky, D. and F. Mahmood (1995) "Feeding the mosquito Aedes aegypti with TMOF and its analogs; effect on trypsin biosynthesis and egg development," *Regulatory Peptides* 57:273–281.; Borovsky et al. (1994) "Characterization and localization of mosquito-gut receptors for trypsin modulating oostatic factor using complementary peptide immunochemistry" *FASEB J.* 8:350–355.). This characteristic permits the testing of TMOF and its analogues by feeding them to mosquito and other pest larvae. To find out if truncated TMOF peptides have an effect on larval growth and development, a series of peptides were synthesized and tested by feeding them to mosquito larvae at concentrations of 0 to 5.0 mg/ml (Table 2). Individual, newly hatched *Aedes aegypti* larvae were maintained in separate microtiter plate wells on a diet of autoclaved yeast (1 mg/ml). The diet was supplemented with TMOF peptides (Table 2). An identical number of larvae maintained on yeast served as a control. Larvae fed on different concentrations of TMOF peptides (0 mg/ml to 5.0 mg/ml) were monitored for eight (8) days for survival and larval growth and development. All control groups survived and larval growth and development was normal. Since larvae swallow only a small portion of the yeast particles adsorbed the peptides, it is assumed that approximately 1 to 20 ng are taken orally at the high concentrations. The results are displayed in Table 2 as the Lethal Dose at 50% mortality ($LD_{50}$) of the TMOF peptides.

Table 1. The Effect of TMOF and its analog peptides on mosquito larvae

TABLE 1

The Effect of TMOF and its analog peptides on mosquito larvae

| Compound | SEQ ID NO | N | $LD_{50}$ + S.E.M. (mM) |
|---|---|---|---|
| 1. YDPAP$_6$ | 7 | 3 | 0.2 ± 0.02 |
| 2. MPDYP$_5$ | 26 | 3 | >3.0 |
| 3. YDPAF | 41 | 3 | 0.33 ± 0.2 |
| 4. YEPAP | 47 | 3 | 0.35 ± 0.02 |
| 5. FDPAP | 24 | 3 | 0.37 ± 0.15 |
| 6. YDPLP | 46 | 3 | 0.5 ± 0.04 |
| 7. YDPAL | 42 | 3 | 0.52 ± 0.03 |
| 8. YAPAP | 51 | 3 | 0.54 ± 0.13 |
| 9. YNPAP | 49 | 3 | 0.55 ± 0.03 |
| 10. (D)YDPAP | 43 | 3 | 0.56 ± 0.03 |
| 11. YFPAP | 48 | 3 | 0.64 ± 0.03 |
| 12. YDPAP | 1 | 3 | 0.64 ± 0.03 |
| 13. YDLAP | 38 | 3 | 0.6 ± 0.05 |
| 14. YDFAP | 36 | 3 | 0.74 ± 0.13 |
| 15. YDAAP | 34 | 3 | 1.0 ± 0.18 |
| 16. YDPGP | 45 | 5 | 1.1 ± 0.18 |
| 17. Y(D)DPAP | 30 | 3 | 1.2 ± 0.3 |
| 18. YSPAP | 52 | 3 | 1.4 ± 0.03 |
| 19. YDPAA | 53 | 3 | 1.6 ± 0.13 |
| 20. YDPFP | 44 | 4 | 1.7 ± 0.4 |
| 21. ADPAP | 15 | 4 | 2.0 ± 0.36 |
| 22. Y(D)DP | 29 | 3 | 0.28 ± 0.01 |
| 23. DPA | 19 | 3 | 0.4 ± 0.03 |
| 24. (D)YDP | 40 | 3 | 0.51 ± 0.05 |
| 25. DAA | 17 | 3 | 0.91 ± 0.06 |
| 26. YDG | 37 | 3 | 0.95 ± 0.11 |
| 27. YDF | 35 | 3 | 0.97 ± 0.11 |
| 28. APA | 16 | 3 | 1.0 ± 0.07 |
| 29. AAP | 13 | 3 | 1.08 ± 0.07 |
| 30. YSF | 50 | 3 | 1.08 ± 0.12 |
| 31. DYP | 21 | 4 | 1.27 ± 0.17 |

TABLE 1-continued

The Effect of TMOF and its analog peptides on mosquito larvae

| Compound | SEQ ID NO | N | $LD_{50}$ + S.E.M. (mM) |
|---|---|---|---|
| 32. YDA | 33 | 3 | 1.6 ± 0.13 |
| 33. FDP | 23 | 3 | 1.98 ± 0.6 |
| 34. YDP | 39 | 5 | 2.3 ± 0.4 |
| 35. FSP | 25 | 3 | 2.3 ± 0.13 |
| 36. YAP | 31 | 3 | 2.3 ± 0.5 |
| 37. PAA | 27 | 3 | 2.4 ± 0.34 |
| 38. PAP | 28 | 3 | 3.17 ± 0.14 |
| 39. FAP | 22 | 3 | 3.8 ± 0.23 |
| 40. ADP | 14 | 3 | >6.6 |
| 41. YD | 32 | 3 | 1.24 ± 0.06 |
| 42. DY | 20 | 3 | 3.0 ± 0.8 |

Groups of 12 to 24 mosquito larvae were incubated with different concentrations of TMOF and its analog peptides in 100 μl microtiter plates for 7 days. Results are expressed as $LD_{50}$ + S.E.M.

5.2 Effect of TMOF Analog Peptides on *Heliothis virescens*

Several analogues were chosen and were fed to fourth instar *Heliothis virescens* for seven (7) days and to first instars for fourteen (14) days (Tables 3 and 4). In both cases a reduction in weight gain and trypsin inhibition was noted (Tables 3 and 4).

Individual first instar and fourth instar larvae of *H. virescens* were maintained in separate plastic cups and were fed on artificial diet blocks on which different concentrations of TMOF (0 to 1.6 mg) were adsorbed. Larvae were fed for 5 to 14 days and larval weight and trypsin activity were measured at the end of the experimental periods. A reduction in larval weight and trypsin biosynthesis was observed in fourth instar larvae that were fed TMOF analogue peptides for 5 days (see Table 3 analogues 15, 14, and 18). When first instar larvae were fed for 14 days, an 18% and 26% reduction in weight was observed when analogues 15 and 16 were used (Table 4). These results indicate that the TMOF peptides of the subject invention control trypsin biosynthesis in *H. virescens* as was shown in mosquitoes and that these analogues can be used to control these agricultural pest insects.

These results indicate that short TMOF peptides can be used efficiently to block larval growth in mosquitos and other pests. An advantage of using short analogs is that they can penetrate the midgut much faster than longer peptides and are less expensive to synthesize by conventional chemical methods. Synthetic organic mimics of these peptides can also be prepared. These organic compounds can penetrate the larval skin and thus, can be used to spray plants for pest control.

TABLE 2

Effect of TMOF analogs on growth and TTLE biosynthesis on fourth Instar *H. virsecens*

| TMOF Analog polypeptide | Weight mg ± S.E.M. Start | Weight mg ± S.E.M. End | Weight Gain (mg) | Trypsin g ± S.E.M. | Inhibition (% ± S.E.M.) |
|---|---|---|---|---|---|
| Control | 35.63 ± 1.54 | 219 ± 8.2 | 183.5 | 2.5 ± 0.15 | 0 |
| DYP(3) | 36.2 ± 2.4 | 216.7 ± 13 | 180.5 | 2.2 ± 0.3 | 14 ± 1.8 |
| YDPGP(9) | 31.7 ± 1.6 | 199.8 ± 11 | 163.1 | 2.1 ± 0.1 | 17 ± 1 |
| YDP(11) | 37 ± 1.5 | 223.4 ± 16 | 186.3 | 2.1 ± 0.3 | 19 ± 3.2 |

TABLE 2-continued

Effect of TMOF analogs on growth and TTLE biosynthesis on fourth Instar *H. virsecens*

| TMOF Analog polypeptide | Weight mg ± S.E.M. Start | End | Weight Gain (mg) | Trypsin g ± S.E.M. | Inhibition (% ± S.E.M.) |
|---|---|---|---|---|---|
| ADAAP(12) | 35.7 ± 1.5 | 209.7 ± 12 | 174.1 | 2.4 ± 0.3 | 5 ± 0.6 |
| YDAAP(15) | 38.2 ± 1.3 | 217 ± 9.5 | 179 | 2.1 ± 0.2 | 17 ± 1.6 |
| YDFAP(16) | 37 ± 1.3 | 201 ± 12 | 164 | 2.1 ± 0.2 | 19 ± 1.5 |
| YSPAP(18) | 30.6 ± 1.2 | 188 ± 10.6 | 151 | 2.0 ± 0.2 | 19 ± 2 |
| Y(D)DPAP(20) | 34.6 ± 2 | 188 ± 12 | 153 | 2.1 ± 0.2 | 15 ± 1.3 |

TABLE 3

Feeding of *H. virescens* on TMOF analogs for 14 day

| TMOF analog | N | Number of Dead Larvae | Weight (mg) ± S.E.M. | Weight Reduction (%) ± S.E.M. |
|---|---|---|---|---|
| Control | 8 | 2 | 163 ± 12 | 0 |
| DYP(3) | 9 | 1 | 149 ± 9 | 9 ± 0.5 |
| YDPGP(9) | 8 | 2 | 153 ± 10 | 6 ± 0.4 |
| YDP(11) | 9 | 0 | 157 ± 10 | 4 ± 0.2 |
| ADMP(12) | 10 | 0 | 141 ± 9 | 7 ± 0.4 |
| YDMP(15) | 10 | 0 | 133 ± 7 | 18 ± 1 |
| YDFAP(16) | 9 | 1 | 121 ± 7 | 26 ± 1.5 |
| YSPAP(18) | 10 | 0 | 168 ± 11 | 0 |
| Y(D)DPAP(20) | 9 | 1 | 152 ± 27 | 7 ± 1 |

Sequence identification numbers for peptides listed in Tables 2 and 3 are as follows: DYP (SEQ ID NO: 21), YDPGP (SEQ ID NO: 45), YDP (SEQ ID NO: 39), ADAAP (SEQ ID NO: 54), YDAAP (SEQ ID NO: 34), YDFAP (SEQ ID NO: 36), YSPAP (SEQ ID NO: 52), and Y(D)DPAP (SEQ ID NO: 30)

Fourth instar larvae were weighed and fed on synthetic food and 0.8 mg of TMOF analogues for 5 days. After feeding, larvae were weighed and guts were removed and groups of 3 to 4 guts were incubated with [$^3$H]DFP and analyzed for trypsin biosynthesis. Results are average of 3 to 10 experiments S.E.M.

5.3 Determination of NPF Affect on Trypsin Biosynthesis

Figure 2:
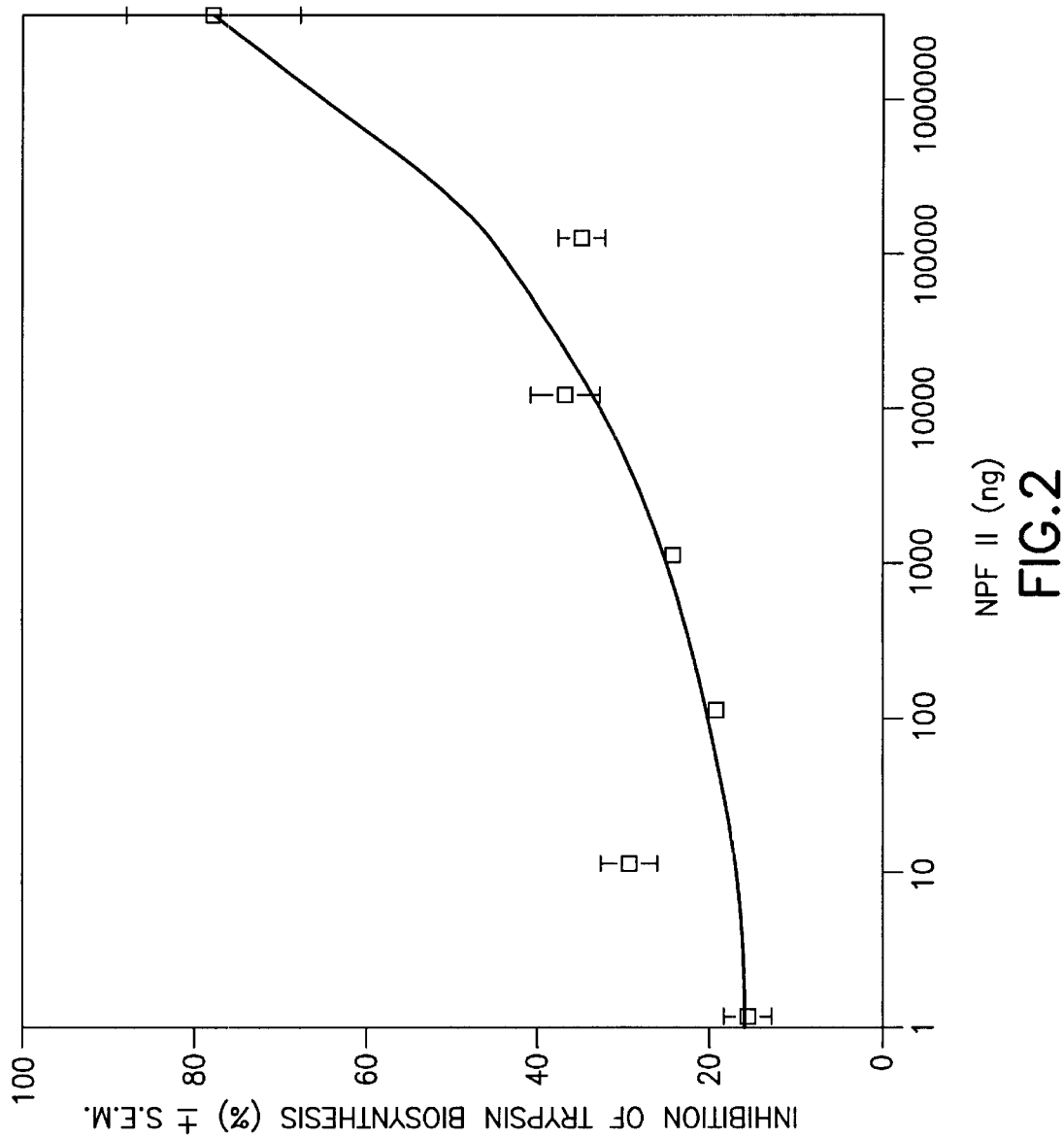
Figure 3:
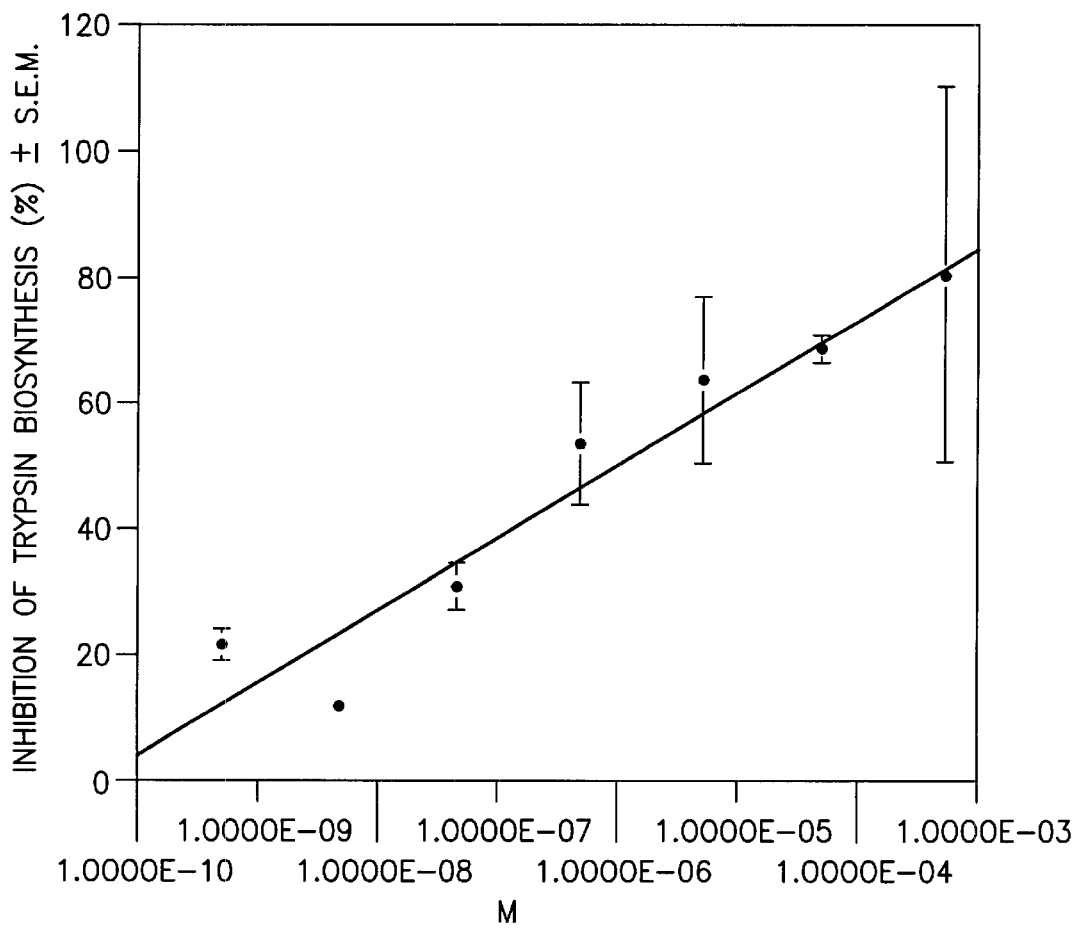

To determine whether NPF I and II affect trypsin biosynthesis in the midgut of female *Aedes aegypti*, females were fed a blood meal and immediately injected with 0.25 µl of the peptide at concentrations of 2.5 µg to 12.5 pg and 30 hours later the midguts were removed and assayed for trypsin biosynthesis (Borovsky et al., 1990 "Mosquito Oostatic Factor: A Novel Decapeptide Modulating Trypsin-Like Enzyme Biosynthesis in the Midgut" FASEB J. 4:3015–3020; Borovsky et al. 1993 "Mass Spectrometry and Characterization of *Aedes aegypti* Trypsin Modulating Oostatic Factor (TMOF) and its Analog" Insect Biochem. Molec. Biol. 23:703–712). Each experiment was repeated 3 times (5 females per group) and the results are expressed as % inhibition of trypsin biosynthesis±S.E.M. (FIG. 1). Fifty percent inhibition of trypsin biosynthesis was achieved at a concentration of $10^{-6}$M NPF I. NPF II was effective at a dose of $10^{-3}$M (78%±10), at $10^{-6}$M NPF II inhibited trypsin biosynthesis by 35% (FIG. 2).

To determine if NPF I releases a neuroendocrine factor from the brain or the thoracic ganglia which in turn may release TMOF from the ovary, female *Aedes aegypti* were fed a blood meal, immediately ligated and injected with different concentrations of NPF I($10^{-3}$M to $10^{-9}$M) in 0.25 µl of sterile distilled water. Thirty hours later, abdomens were removed and 3 groups of 5 abdomens per NPF concentration were assayed for trypsin biosynthesis (Borovsky et al., 1990, 1993). Fifty-four percent inhibition was achieved with $10^{-6}$M of NPF I indicating that NPF I affects trypsin biosynthesis in the gut by binding to a TMOF receptor and not by the release of neuroendocrine factors from the brain or the thoracic ganglia that in turn release TMOF from the ovary. Because the structure of NPF I is different from TMOF it appears that NPF I does not bind to TMOF specific binding site on the gut receptor but to a different site on the same or different receptor.

5.4 Cytoimmunochemical Analysis of Mosquito Gut After Blood Meal

Cytoimmunochemical analysis of the mosquito gut after the blood meal using antiserum against NPF I revealed that exocrine cells with NPF I-like molecules are synthesized by the mosquito epithelial cells 24 hours after a blood meal. In females that did not take a blood meal these cells are not found. Thus, it is possible that NPF I is a secondary signal in a cascade of signals that starts with the release of TMOF from the ovary, the hormone then binds to a TMOF gut receptor (Borovsky et al., 1994) that stimulates the synthesis and release of NPF I from gut specific exocrine cells. NPF I binds to a receptor site on the gut. The binding site may be adjacent to or part of the TMOF receptor and causes the cessation of trypsin biosynthesis.

5.5 Bioassays for NPF Activity Against Lepidopteron and Coleopterans

Biological activity of the pest control compounds of the subject invention can be confirmed using standard bioassay procedures. One such assay is the budworm-bollworm (*Heliothis virescens* [Fabricius] and *Helicoverpa zea* [Boddie]) assay. Lepidoptera bioassays can be conducted with either surface application to artificial insect diet or diet incorporation of samples. All Lepidopteran insects can be tested from the neonate stage to the second instar. All assays can be conducted with either toasted soy flour artificial diet or black cutworm artificial diet (BioServ, Frenchtown, N.J.).

Diet incorporation can be conducted by mixing the samples containing the pest-icontrol compound with artificial diet at a rate of 6 mL suspension plus 54 mL diet. After vortexing, this mixture is poured into plastic trays with compartmentalized 3-ml wells (Nutrend Container Corporation, Jacksonville, Fla.). A water blank containing no pest control compound serves as the control. First instar larvae (USDA-ARS, Stoneville, Miss.) are placed onto the diet.mixture. Wells are then sealed with Mylar sheeting (ClearLam Packaging, Ill.) using a tacking iron, and several pinholes are made in each well to provide gas exchange. Larvae can be held at 25° C. for 6 days in a 14:10 (light:dark) holding room. Mortality and stunting are then recorded after six days.

Bioassay by the top load method utilizes the same sample and diet preparations as listed above. The samples are applied to the surface of the insect diet. In a specific embodiment, surface area can range from 0.3 to approximately 0.8 cm² depending on the tray size; 96 well tissue culture plates can be used in addition to the format listed above. Following application, samples are allowed to air dry before insect infestation. A water blank containing no control compound can serve as the control. Eggs are applied to each treated well. The wells are then sealed with Mylar sheeting (ClearLam Packaging, Ill.) using a tacking iron, and pinholes are made in each well to provide gas exchange. Bioassays are held at 25° C. for 7 days in a 14:10 (light:dark) or 28° C. for 4 days in a 14:10 (light:dark) holding room. Mortality and insect stunting are recorded at the end of each bioassay.

Another assay useful according to the subject invention is the Western corn rootworm assay. Samples can be bioassayed against neonate western corn rootworm larvae (*Diabrotica virgifera virgifera*) via top-loading of the pest control sample onto an agar-based artificial diet at a rate of 160 ml/cm². Artificial diet can be dispensed into 0.78 cm² wells in 48-well tissue culture or similar plates and allowed to harden. After the diet solidifies, samples are dispensed by pipette onto the diet surface. Excess liquid is then evaporated from the surface prior to transferring approximately three neonate larvae per well onto the diet surface by camel's hair brush. To prevent insect escape while allowing gas exchange, wells are heat-sealed with 2-mil punched polyester film with 27HT adhesive (Oliver Products Company, Grand Rapids, Mich.). Bioassays are held in darkness at 25° C., and mortality scored after four days.

Analogous bioassays can be performed by those skilled in the art to assess activity against other pests, such as the black cutworm (*Agrotis ipsilon*).

5.6 Target Pests

Toxins of the subject invention can be used, alone or in combination with other toxins, to control one or more non-mammalian pests. These pests may be, for example, those listed in Table 1. Activity can readily be confirmed using the bioassays provided herein, adaptations of these bioassays, and/or other bioassays well known to those skilled in the art.

TABLE 2

Target Pest Species

| ORDER/Common Name | Latin Name |
| --- | --- |
| LEPIDOPTERA | |
| European Corn Borer | *Ostrinia nubilalis* |
| European Corn Borer resistant to Cry1A | *Ostrinia nubilalis* |
| Black Cutworm | *Agrotis ipsilon* |
| Fall Armyworm | *Spodoptera frugiperda* |
| Southwestern Corn Borer | *Diatraea grandiosella* |
| Corn Earworm/Bollworm | *Helicoverpa zea* |
| Tobacco Budworm | *Heliothis virescens* |

TABLE 2-continued

Target Pest Species

| ORDER/Common Name | Latin Name |
| --- | --- |
| Tobacco Budworm Rs | *Heliothis virescens* |
| Sunflower Head Moth | *Homeosoma ellectellum* |
| Banded Sunflower Moth | *Cochylis hospes* |
| Argentine Looper | *Rachiplusia nu* |
| Spilosoma | *Spilosoma virginica* |
| Bertha Armyworm | *Mamestra configurata* |
| Cabbage Looper | *Trichlopusia ni* |
| Diamondback Moth | *Plutella xylostells* |
| COLEOPTERA | |
| Red Sunflower Seed Weevil | *Smicronyx fulvus* |
| Sunflower Stem Weevil | *Cylindrocopturus adspersus* |
| Sunflower Beetle | *Zygoramma exclamationis* |
| Canola Flea Beetle | *Phyllotreta cruciferae* |
| Western Corn Rootworm | *Diabrotica virgifera virgifera* |
| DIPTERA | |
| Hessian Fly | *Mayetiola destructor* |
| HOMOPTERA | |
| Greenbug | *Schizaphis graminum* |
| HEMIPTERA | |
| Lygus Bug | *Lygus lineolaris* |
| NEMATODA | |
| Soybean Cyst Nematode | *Heterodera glycines* |

5.7 Insertion of Polynucleotides Encoding Pesticidal Polypeptides Into Plants One aspect of the subject invention is the transformation of plants with genes encoding the insecticidal toxin of the present invention. The transformed plants are resistant to attack by the target pest.

Genes encoding pesticidal polypeptides, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the Bacillus toxin can be inserted into the vector at a suitable restriction site. The resulting plasmid is used to transform *E. coli*. The *E. coli* cells are cultivated in a suitable nutrient medium, then harvested and lysed, the plasmid is recovered. Sequence analysis, restriction analysis, electrophoresis, and other biochemical and/or molecular biological methods are generally carried out as methods of analysis. After each manipulation, the DNA sequence used can be cleaved and joined to the next DNA sequence. Each plasmid sequence can be cloned in the same or other plasmids. Once the inserted DNA has been integrated in the genome, it is relatively stable there and, as a rule, does not come out again. It normally contains a selection marker that confers on the transformed plant cells resistance to a biocide or an antibiotic, such as kanamycin, G418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. These techniques include transformation with T-DNA ("transferred DNA"; discussed in more detail below) using *Agrobacterium tumefaciens* or *Agrobacterium rhizogenes* as transformation agent, fusion, injection, biolistics (microparticle bombardment), or electroporation and other methods known to those of skill in the art.

One of the most widely used approaches for the introduction of DNA into plant cells exploits the natural DNA-transferring properties of *Agrobacterium tumefacients* and *Agrobacterium rhizogenes*, the two species which cause crown gall and hairy root. Their ability to cause disease depends on the presence of large plasmids, in excess of 100 kb, which are referred to as the "Tumour-inducing" or (Ti) and "Root-inducing" (or Ri) plasmids respectively.

A region referred to as the T-DNA ("Transferred DNA") is transferred from an infecting Agrobacterium cell into the nucleus of the plant cell, where it is integrated into the plant genome. Transfer of the T-DNA depends on a set of genes called vir if they are on the Ti plasmid, or chv if they are on the chromosome. These genes are induced in response to various compounds in exudates from wounded plants. The T-DNA itself is flanked by repeated sequences of around 25 base pairs, called border repeats (or left and right borders). The T-DNA contains a group of genes referred to as the onc genes, which are responsible for the oncogenicity of the T-DNA.

The use of Agrobacterium in the genetic manipulation of plants involves the insertion of foreign DNA into the T-DNA of a bacterial cell and subsequent transfer of the DNA by the transformed bacterium into the plant. As long as the necessary proteins are provided by the bacterium, any sequences flanked by the T-DNA border repeats can be transferred into the recipient plant cell genome. The Ti plasmids are too large to manipulate directly, but this problem can be circumvented by using cointegrative and binary systems.

The two main components of a cointegrative system are a Ti plasmid that has typically been modified by the replacement of material between the border repeats (including the onc sequences) by pBR322; and a intermediate vector, which is a modified pBR322 containing an extra marker, such as kanamycin resistance. The gene to be introduced into the target plant is first cloned in to the intermediate vector, and this construct is then introduced into Agrobacterium containing the Ti vector. The pBR322-based plasmid cannot replicate efficiently inside Agrobacterium, so selection for kanamycin resistance identifies those Agrobacterium cells where the pBR322-based intermediate plasmid has been integrated by homologous recombination into the Ti plasmid. Because the recombination is homologous, it will take place across the pBR322 sequences and therefore result in integration between the border repeats.

The need for cointegration of the plasmids can be circumvented by use of a binary vector, such as pBinl9, a small plasmid containing a pair of left and right borders. The lacZ region, located within the borders, facilitates insertion and detection of DNA. A neomycin phosphotransferase gene, typically modified for expression in plants by addition of nopalline synthase expression sequences, is also present within the borders. Outside the left and right borders, there is typically a kanamycin resistance gene that will function in prokaryotes and a broad host-range origin derived from the plasmid pRK252. The proteins that catalyze transfer of the T-DNA into the host plant do not have to be cis-encoded (i.e., do not have to be encoded by the same molecule). Therefore, if the binary vector is introduced into Agrobacterium that already contains a resident Ti plasmid, the resident plasmid can provide all the functions needed to transfer into a plant nucleus the DNA between the borders of the binary vector.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A pesticidal composition comprising:
   (a) a first part consisting of the pesticidal peptide Tyr-Asp-Pro-Ala-Phe (SEQ ID NO: 41) and a pesticidally acceptable carrier; and
   (b) a second part comprising a pest attractant and a pesticidally acceptable carrier.

2. The pesticidal composition of claim 1 wherein the N-terminus of said polypeptide is acetylated and/or the C-terminus of said polypeptide is amidated.

3. The pesticidal composition of claim 1 wherein the polypeptide is bound to a lipid or other carrier molecule.

4. The pesticidal composition of claim 1 comprising one or more D-amino acids.

5. The pesticidal composition of claim 1 wherein the polypeptide is covalently attached to a heterologous protein to form a fusion protein.

6. The pesticidal composition of claim 1, wherein the attractant includes at least one attractant species selected from the group consisting of: (Z)-11,12-hexadecadienal; 1-octen-3-ol (octenol); anethole; carbon dioxide; cis-11-hexadecenal; cis-11-tetradecenyl acetate; cis-3,cis-13-octadecadienyl acetate; cis-7,8-epoxy-2-methyloctadecane; cis-7,cis-11-hexadecadienyl acetate (with cis-7,trans-11); cis-7,cis-11-hexadecadienyl acetate (with cis-7,trans-11); cis-7-dodecenyl acetate; cis-8-dodecenyul acetate; cis-9,trans-11-tetradecadienyl acetate (with cis-9,trans-12); cis-9,trans-12-tetradecadienyl acetate; cis-9-dodecenyl acetate; cis-9-tetradecenal (with cis-11-hexadecenal); cis-9-tetradecenyl acetate; dibutyl succinate; dimethyl disulfide; ethyl dimethylisobutyl-cyclopropane carboxylate; ethyl ester of 2-methyl-3-pentenoic acid; eugenol; isoamyl salicylate; lavender absolute; N,N-diethyl-m-toluamide; phenethyl propionate; pheromones; propyl benszodioxancarboxylate; trans-11-tetradecenal; trans-11-tetradecenyl acetate (with cis-11); trans-3,cis-13-octadecadienyl acetate and trans-8,trans-10-dodecadienol.

7. The pesticidal composition of claim 1 formulated as a compositional form selected from the group consisting of: sprays, encapsulations, granulations, powders, liquids, solutions, suspensions, pellets, briquettes, bricks, foams, gels, suspensions, pastes and emulsifiable concentrates.

8. The pesticidal composition of claim 1 formulated as a slow-release formula.

9. The pesticidal composition of claim 8 in a form selected from the group consisting of pellets, briquettes and bricks.

10. The pesticidal composition of claim 8 in the form of pellets.

11. The pesticidal composition of claim 8 formulated to float in an aqueous medium.

12. The pesticidal composition of claim 8 formulated to reside at a depth of 0 to 2 feet below the surface of an aqueous medium.

13. The pesticidal composition of claim 8 formulated to sink in an aqueous medium.

14. A pesticidal composition comprising:
(a) a first part comprising a pesticidal peptide and a pesticidally acceptable carrier, wherein the pesticidal peptide consists of the amino acid sequence Tyr-Asp-Pro-Ala-Phe (SEQ ID NO:4 1); and
(b) a second part comprising a pest attractant and a pesticidally acceptable carrier.

15. A method of preventing, reducing or eliminating infestation of a geographical area by an insect population, comprising:
(a) applying to a pest-inhabited locus of the geographical area the pesticidal peptide Tyr-Asp-Pro-Ala-Phe (SEQ ID NO: 41) and a pesticidally acceptable carrier; and
(b) applying a pest attracting amount of a pest attractant and a pesticidally acceptable carrier in the proximity of the pesticidal composition such that pests are attracted to the pesticidal composition,
wherein infestation of a geographical area by pests is prevented, reduced, or eliminated.

16. The method of claim 15 wherein the first and second steps are performed simultaneously.

17. The method of claim 15 wherein the first and second steps are performed sequentially in any order.

18. The method of claim 15 wherein the pest regulates biosynthesis of trypsin and trypsin-like enzymes through binding of a ligand to an insect gut receptor of said insect.

19. The method of claim 15 wherein the pest is selected from the group consisting of mosquitoes, flesh flies, fleas, sand flies, house flies, and dog flies.

20. The method of claim 15, wherein the attractant includes at least one attractant species selected from the group consisting of: (Z)-11,12-hexadecadienal; 1-octen-3-ol (octenol); anethole; carbon dioxide; cis-11-hexadecenal; cis-11-tetradecenyl acetate; cis-3,cis-13-octadecadienyl acetate; cis-7,8-epoxy-2-methyloctadecane; cis-7,cis-11-hexadecadienyl acetate (with cis-7,trans-11); cis-7-dodecenyl acetate; cis-8-dodecenyul acetate; cis-9,trans-11-tetradecadienyl acetate (with cis-9,trans-12); cis-9,trans-12-tetradecadienyl acetate; cis-9-dodecenyl acetate; cis-9-tetradecenal (with cis-11-hexadecenal); cis-9-tetradecenyl acetate; dibutyl succinate; dimethyl disulfide; ethyl dimethylisobutyl-cyclopropane carboxylate; ethyl ester of 2-methyl-3-pentenoic acid; eugenol; isoamyl salicylate; lavender absolute; N,N-diethyl-m-toluamide; phenethyl propionate; pheromones; propyl benszodioxancarboxylate; trans-11-tetradecenal; trans-11-tetradecenyl acetate (with cis-11); trans-3,cis-13-octadecadienyl acetate and trans-8,trans-10-dodecadienol.

21. The method of claim 15 wherein the pest inhabited locus is a body of water.

22. The method of claim 21 wherein the body of water is inhabited by mosquito larvae.

23. The method of claim 15 wherein the pesticidal peptide and the attractant are provided in a unitary formulation.

24. The method of claim 22 wherein the unitary formulation is in a form selected from the group consisting of pellets, briquettes, sprays, bricks, powders, pastes, gels, soluble powders, dusting agents and granules.

25. The method of claim 22 wherein the unitary formulation is a continuous time-release formulation.

26. The method of claim 24 wherein the unitary formulation floats on water.

27. The pesticidal composition of claim 24 formulated to reside at a depth of 0 to 2 feet below the surface of water.

28. The pesticidal composition of claim 24 formulated to sink in an aqueus medium.

29. The method of claim 15 wherein the pesticidal polypeptide is administered in association with a pest food.

30. The method of claim 15 wherein the pest is an insect species selected from the group consisting of: *Aedes aegypti, Culex quinquefasciatus, Anopheles albimanus, Anopheles quadrimaculatus, Lutzomyia anthrophora, Culicoides variipennis, Stomoxys calcitrans, Musca domestics, Ctenocephalides felis*, and *Helothis virescens*.

31. The method of claim 15 wherein the pest is an insect selected from the group consisting of coleopterans, lepidopterans, and dipterans.

32. The method of claim 15 wherein the pest is a blood-sucking insect.

33. The method of claim 15 wherein the pest is a blood-sucking insect of the order Diptera.

34. The method of claim 15 wherein the pest is a blood-sucking insect of the suborder Nematocera.

35. The method of claim 15 wherein the pest is a blood-sucking insect of the family Culcidae.

36. The method of claim 15 wherein the pest is a blood-sucking insect of a subfamily selected from the group consisting of Culicinae, Corethrinae, Ceratopogonidae and Simuliidae.

37. The method of claim 15 wherein the pest is a blood-sucking insect of a genus selected from the group consisting of Culex, Theobaldia, Aedes, Anopheles, Forciponiyia, Culicoides and Helea.

38. The method of claim 15 wherein the pest is a mosquito.

* * * * *